(12) United States Patent
Goodman et al.

(10) Patent No.: US 7,326,561 B2
(45) Date of Patent: Feb. 5, 2008

(54) FLOW-THRU CHIP CARTRIDGE, CHIP HOLDER, SYSTEM AND METHOD THEREOF

(76) Inventors: Jack Goodman, 1415 Crab House Rd., Lusby, MD (US) 20657; Matthew Torres, 106 Nut Bush Ct., Hillsborough, NC (US) 27278; Hongjun Yang, 19217 Wheatfield Dr., Germantown, MD (US) 20876; David G. Mateer, 7791 Nikau Dr., Niwot, CO (US) 80503; Ian Stuart Richard Smith, 4715 Tally Ho Ct., Boulder, CO (US) 80301-2864

( * ) Notice: Subject to any disclaimer, the term of this patent is extended or adjusted under 35 U.S.C. 154(b) by 836 days.

(21) Appl. No.: 09/926,094

(22) PCT Filed: Dec. 20, 2000

(86) PCT No.: PCT/US00/34535

§ 371 (c)(1),
(2), (4) Date: Nov. 12, 2003

(87) PCT Pub. No.: WO01/45843

PCT Pub. Date: Jun. 28, 2001

(65) Prior Publication Data

US 2004/0137604 A1 Jul. 15, 2004

Related U.S. Application Data

(60) Provisional application No. 60/171,510, filed on Dec. 22, 1999.

(51) Int. Cl.
*C12M 1/36* (2006.01)

(52) U.S. Cl. .............................. 435/286.5; 435/287.2; 435/288.3; 435/288.6
(58) Field of Classification Search ............ 435/286.5, 435/287.2, 288.1, 288.3, 288.6
See application file for complete search history.

(56) References Cited

U.S. PATENT DOCUMENTS

| | | | | | |
|---|---|---|---|---|---|
| 4,294,924 | A | * | 10/1981 | Pepicelli et al. | 435/30 |
| 6,194,160 | B1 | * | 2/2001 | Levin | 435/7.1 |
| 6,303,389 | B1 | * | 10/2001 | Levin et al. | 436/518 |
| 6,458,584 | B1 | * | 10/2002 | Mirzabekov et al. | 435/287.2 |
| 2003/0044777 | A1 | * | 3/2003 | Beattie | 435/6 |

* cited by examiner

*Primary Examiner*—David Redding
(74) *Attorney, Agent, or Firm*—Blank Rome, LLP

(57) ABSTRACT

A system for performing hybridization assays comprises a cartridge for housing a flow through device, where the cartridge includes a test fluid chamber for facilitating a substantially uniform flow of a test fluid mixture through the flow through device, and a fluidics station to deliver the test fluid mixture to the cartridge. The cartridge has a chip holder that holds the flow-through device, which has an array of microchannel passages. The chip holder has a support for placement of the flow though device, the test fluid chamber for directing a substantially uniform flow of a test fluid mixture through the array of microchannel passages of the flow through device, and a first port that receives the test fluid mixture. The cartridge has a sealing system for preventing the leakage of the test fluid around the flow through device. The test fluid chamber is defined in part by a spade-like surface having an inlet for the test fluid mixture.

42 Claims, 13 Drawing Sheets

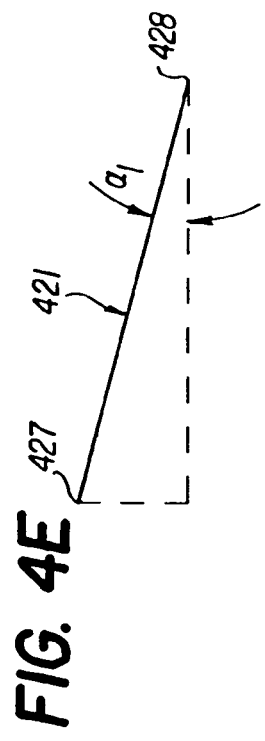
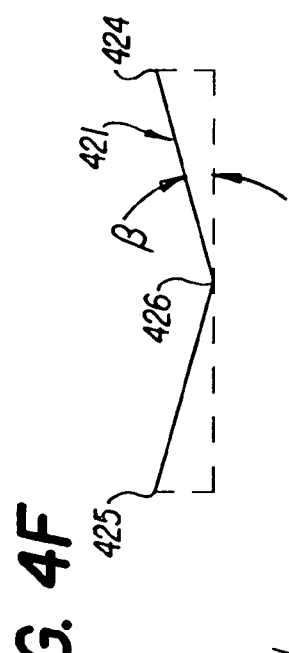
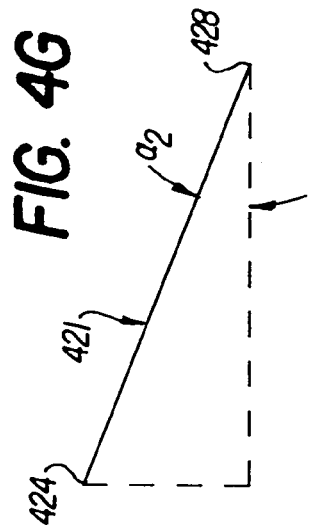
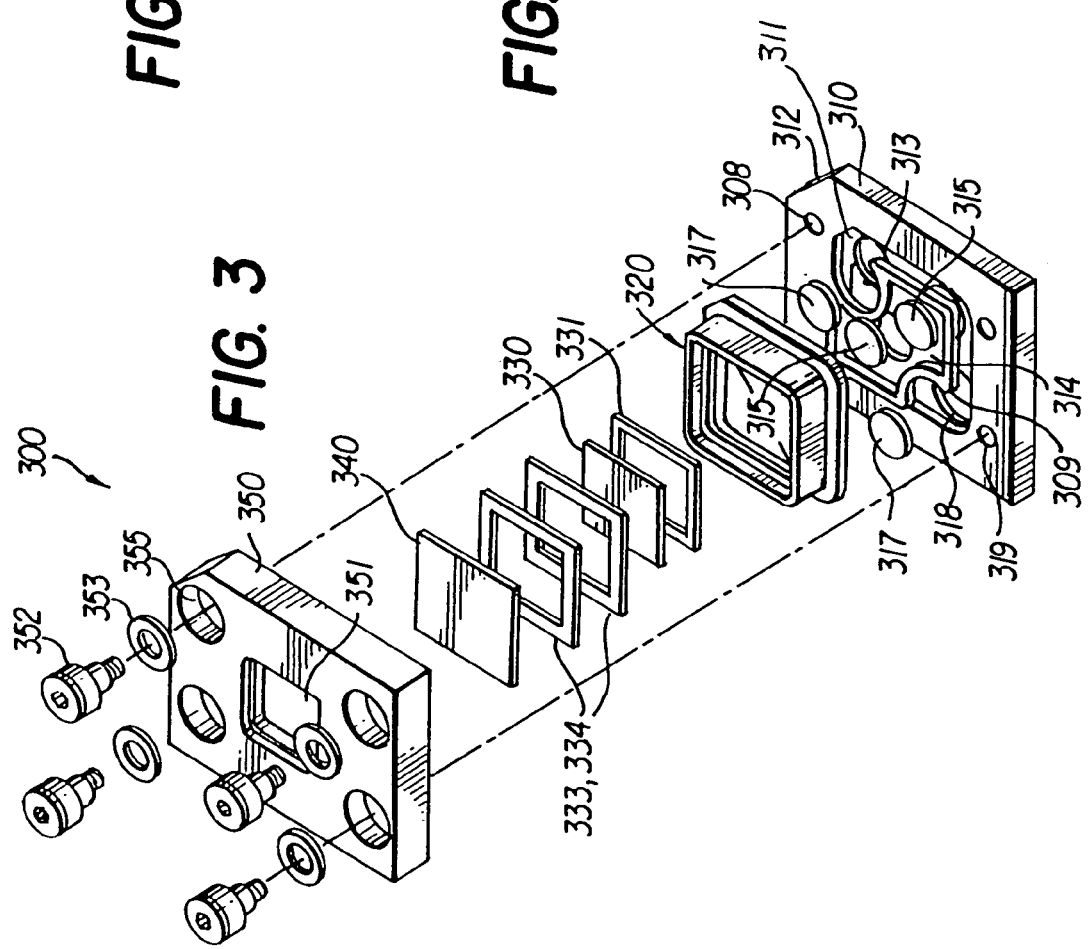

FLOW-THRU CHIP CARTRIDGE, CHIP HOLDER, SYSTEM AND METHOD THEREOF

The present application claims the benefit of the filing date of U.S. Provisional Application No. 60/171,510, filed on Dec. 22, 1999, which is hereby incorporated by reference in its entirety.

BACKGROUND

Microfabrication technology has revolutionized the electronics industry. This unleashed numerous industrial applications in miniaturization and automation of manufacturing processes. The impact of microfabrication technology in biomedical research can be seen in the growing presence of microprocessor-controlled analytical instrumentation and robotics in the laboratory, which is particularly evident in laboratories engaged in high throughput genome mapping and sequencing. One area of particular-interest is the development and use of microfabricated genosensor devices for biomolecule analysis, such as a FLOW-THRU CHIP™ ("FTC").

Microfabricated genosensor devices are compact, but with a high density of components. Known microfabricated binding devices typically are rectangular wafer-type apparatuses with a surface area of approximate one $cm^2$ (1 cm×1 cm). The bounded regions on such devices are typically present in a density of $10^2$-$10^4$ regions/$cm^2$, although the desirability of constructing apparatuses with much higher densities has been regarded as an important objective. As in membrane hybridization, the detection limit for hybridization on flat-surface genosensors is limited by the quantity of DNA that can be bound to a two dimensional area. Another limitation of these approaches is the fact that a flat surface design introduces a rate-limiting step in the hybridization reaction, i.e., diffusion of target molecules over relatively long distances before encountering complementary probes on the surface. A conventional flat surface design substrate is seen in U.S. Pat. No. 5,445,934.

The FTC, which is a recent development, is a flow-through device that comprises a substrate containing first and second sides or surfaces, having a multiplicity of discrete channels extending through the-substrate from the first side to the second side. A schematic example of the FTC is shown in FIG. 1. The FTC 10 includes an ordered array of microscopic channels 13, such as channel 15 shown in greater detail, that transverse the thickness of the substrate. The FTC is particularly useful in that arrays of binding reagents, such as oligonucleotide probes, nucleic acids, and/or antibodies can be immobilized in the channels of the FTC, in spots that incorporate several microchannels. The term "probe" is used to describe a species immobilized within the microchannels and has some specific interaction with a "target" that is part of the fluid test mixture.

A major advantage of the FTCs is the uniformity of the array of microchannels and the uniformity of the individual microchannels. This characteristic distinguishes the FTCs from other three-dimensional arrays, such as porous aluminum oxide, which utilizes non-uniform hole sizes (and thus variable surface areas) and prevents straightforward normalization of results.

The FTC design allows multiple determinations to be carried out in parallel. U.S. Pat. No. 5,843,767, the entire disclosure of which is incorporated herein by reference, describes a microfabricated apparatus for conducting a multiplicity of individual and simultaneous binding reactions. The FTC design facilitates fluid flow therethrough so that biological recognition can occur within the confined volumes of the microchannels. The FTC can also be used in a variety of ways, such as a micro-reactor, concentrator, and micro-cuvette.

In practice, however, a conventional technique of holding and utilizing FTCs has led to several problems. For example, one technique of performing a hybridization assay utilizing the FTC entails placing the FTC on a small series of wells in a vacuum manifold, then placing the fluid test mixture onto the top surface thereof. Vacuum creates fluid flow. This technique, however, leads to substantial leakage problems.

Another conventional technique entails placing the FTC in a container of fluid and relying on diffusion to create the fluid flow through the microchannels. While initial capillary action draws fluid into the microchannels, blockage problems can quickly decrease the flow rate. Further, utilizing this technique is disadvantageous in that the flow rate is not selectively controllable.

Some conventional gene chip array holders (or cartridges) are commercially available. For example, a gene chip array holder is available from AFFYMETRIX. This gene chip array holder, however, operates with a non flow-through substrate. In other words, this conventional cartridge does not facilitate uniform flow during the passage of fluid through the flow-through device. Therefore, this type of conventional design is inadequate to address fluid flow and leakage issues.

SUMMARY OF THE INVENTION

The present invention relates to a chip holder, a cartridge embodying the chip holder, a system embodying the cartridge, and a method thereof.

The chip holder has a body, a flow surface, a test fluid chamber, and a first port. The body has a support that can support a flow though device, which has a first side, a second side, and an array of microchannel passages extending through the first and second sides. The flow surface is formed within the body and is adapted to face the first side (i.e., the flow surface faces the first side when the flow through device is mounted). The test fluid chamber can be defined at least by the flow surface and the first side, and is configured to produce a substantially uniform flow of a test fluid mixture through the microchannel passages. The first port communicates with the test fluid chamber for passing the test fluid mixture into the test fluid chamber.

The flow surface of the chip holder can be angled. The flow surface can include a trench that is sloped relative to the first side, from a first portion to a second portion of the flow surface, to provide a greater spacing at the first portion than at the second portion from the first side. The first port can be formed at the first portion and the trench can have a slope of about 1° to about 4° relative to the first side. More specifically, the slope can be about 2.55° relative to the first side.

The chip holder body further has a second port for draining the test fluid mixture that has passed through the flow through device. The chip holder support can comprise a first shelf disposed around the flow surface, with the support adapted to seat a seal, which can be sandwiched between the first side and the first shelf. The chip holder body can further include a second shelf disposed around the first shelf for seating an observation window.

Further, the chip holder body can include a recess formed on an opposite side of the flow surface. The recess can form a thermal chamber for controlling the temperature of the test fluid in the test fluid chamber.

The cartridge according to the present invention can include a flow through device, such as the one described above, supported on the support, and a chip holder for holding the flow through device, such as the chip holder described previously. The flow through device can be a FLOW-THRU-CHIP™. The cartridge can further include a base for supporting the chip holder. The cartridge can also include a first seal contacting the first side to prevent leakage of the test fluid in the test fluid chamber. The first seal can contact a perimeter region of the flow through device on the first side to direct flow of the test fluid mixture through the flow through device and can prevent leakage of the test fluid mixture around the flow through device. The cartridge can include first and second seals in contact with perimeter regions of the first and second sides of the flow through device to prevent leakage of the test fluid mixture. The first and second seals can be made of Viton rubber. The second seal can have a channel to direct a flow of the test fluid mixture to the second port.

The cartridge can include an observation window, which can be supported on the body, such as the second shelf, for viewing the second side of the flow through device. The window can be a low scatter window disposed over the second side of the flow through device. The cartridge can further include a cover with an opening positioned over the second side for passage of an optical signal therethrough. The cover, the base, and the chip holder all can be constructed from a metal coated with a low light scattering coating. Alternatively, the base, the chip holder, and the cover can be injection molded as one piece. The base can be coupled to the cover with a fastener. The fastener can comprise a plurality of shoulder screws and spring washers. The base can have complementary threaded portions for receiving threaded portions of the shoulder screws. Alternatively, the fastener can comprise a latch, with the cover and the base hinged opposite the latch.

The base can have a recess for receiving the chip holder. The recesses of the body and the base can form a thermal chamber for controlling the temperature of the test fluid in the test fluid chamber. The cartridge can further include an insert positioned in the recesses to further define the thermal chamber. The insert can isolate the thermal fluid within the thermal chamber to prevent the test fluid from contamination. The recess of the base can be complementary to a low-end portion of the chip holder. The cartridge can also include means for distributing a thermal fluid into the thermal chamber. The cartridge can also include a fluid delivery mechanism for delivering the test fluid mixture through the first port.

The system for performing hybridization assays according to the present invention can include the cartridge described previously and a fluidics station for delivering the test fluid mixture to the cartridge. The system can also include a temperature controller for controlling the temperature of the test fluid in the test fluid chamber. The fluidics station can comprise a pump for moving fluid through a fluid path, a buffer selection valve for controlling a passage of buffer solutions from buffer reservoirs, a sample injection valve for controlling the passage of a target or probe compound into the fluid path to form the test fluid mixture, and a re-circulation control valve in the fluid path and communicating with the buffer selection valve for controlling fluid flow. The recirculation valve can be switched between an open circuit mode and a closed circuit mode. In the open circuit mode, the pump communicates with one or more of the buffer solutions to direct the buffer solutions through the sample injection valve and the cartridge. In the closed circuit mode, the pump flows the test fluid flow through the sample injection valve and the cartridge in a closed loop. The system can further include a system controller for monitoring and controlling fluid delivery, timing, and temperature of the system.

The method of performing a hybridization assay according to the present invention comprises the steps of controlling a passage of buffer solution from a buffer reservoir into the chip cartridge, such as the ones described above, controlling the passage of a target or probe compound into the buffer solution to form the test fluid mixture, and circulating the test fluid mixture to the cartridge in a closed loop.

BRIEF DESCRIPTION OF THE DRAWINGS

These and other features, aspects, and advantages of the present invention will become more apparent from the following description, appended claims, and accompanying exemplary embodiments shown in the drawings, which are briefly described below.

FIG. 3 shows an exploded detailed view of an exemplary embodiment of an FTC cartridge according to the present invention.

FIGS. 4A-4G show detailed views of an FTC holder incorporated in the FTC cartridge of FIG. 3.

FIG. 19 shows an alternative fluidics station that can reverse the flow through the FTC cartridge.

DETAILED DESCRIPTION

Figure 1:
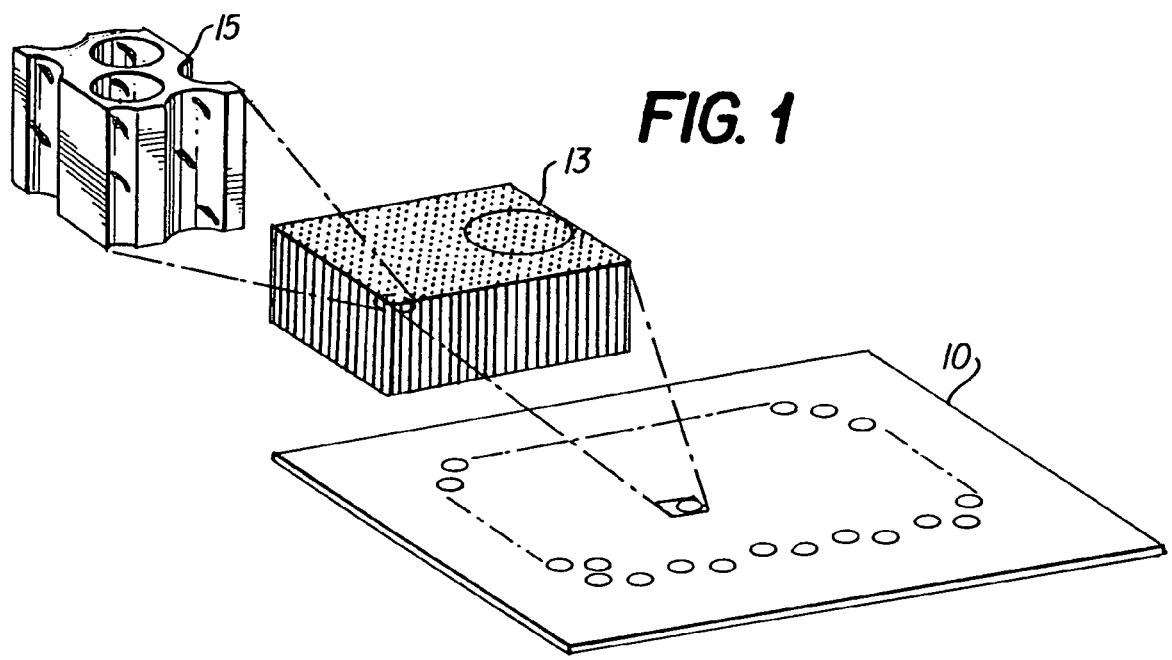
FIG. 1 show a schematic representation of a conventional FTC.
Figure 2:
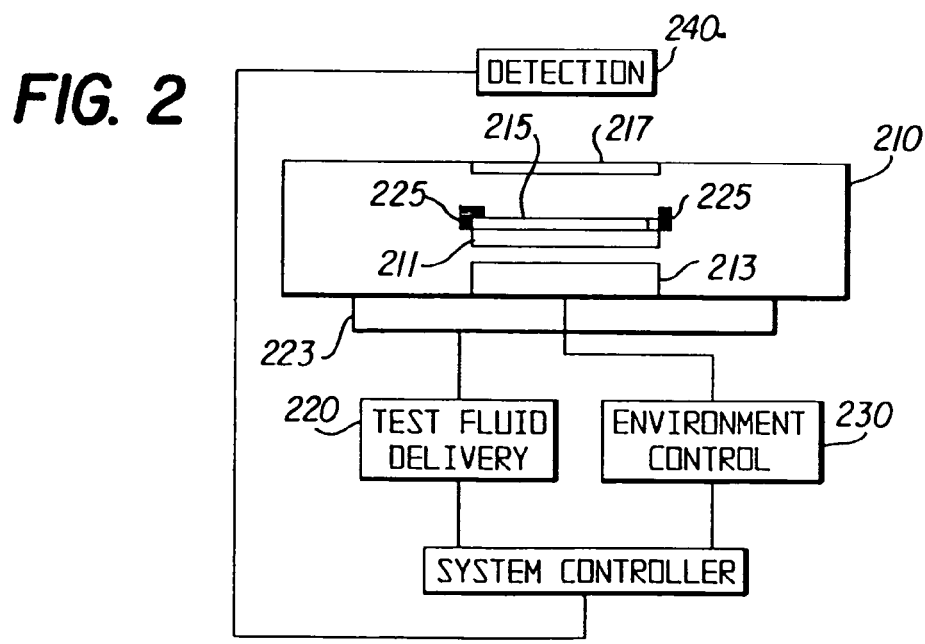
FIG. 2 shows a schematic diagram of an automated hybridization assay system according to the present invention.

FIG. 2 shows a schematic diagram of an automated hybridization assay system 200, which uses an FTC cartridge 210/300. The assay system 200 further includes a test fluid delivery system 220, an environment control unit 230, a detection system 240, and a system controller 250.

The FTC cartridge 210 has one side of an FTC 215 facing an internal test fluid chamber 211, which is designed to provide a uniform flow of a test fluid mixture through the microchannels of the FTC 215. The FTC cartridge 210 also includes a port assembly 223 for communicating test fluid mixtures to and from the FTC 215 and the test fluid delivery system 220, such as the fluidics station illustrated in FIG. 11. The FTC cartridge 210 can further include a temperature control chamber 213 to control the temperature of the test fluid mixture in the test fluid chamber 211 by heat transfer. Temperature control during hybridization provides advantages for nucleic acid analyses, as would be understood by those of skill in the art. Temperature control chamber 213 can be coupled to the environment control unit 230, which can monitor and alter the environmental conditions in the test fluid chamber 211.

The FTC cartridge 210 can also include a sealing mechanism 225 that minimizes test fluid leakage and maximizes fluid flow through the FTC's microchannels. Further, the FTC cartridge 210 includes a window 217 to permit in situ observation from a detection system 240, which can include real-time detection. Real-time hybridization detection can be useful for assay optimization, DNA melting studies, and kinetics-based gene expression analysis.

The system controller 250, coupled to the test fluid delivery system 220, the detection system 240, and the environmental control system 230, can control and monitor a hybridization assay. The detection system 240 can include microfabricated optical and electronic detection components, film devices, charge-coupled-device arrays, camera systems, and phosphor storage devices that are known in the art. The test fluid delivery system 220, which can be, for example, a fluidics station 800 shown in FIG. 11, includes a pump and one or more valves coupled to buffers and test fluid mixtures that provide a controlled flow of a test fluid mixture to the FTC cartridge 210. In addition, the test fluid delivery system 220 can be further designed to circulate pre-test and post-test cleansing fluids for multiple assay applications. Advantageously, the flow through devices can be reused in the FTC cartridge 210 according to the present invention.

Figure 7:
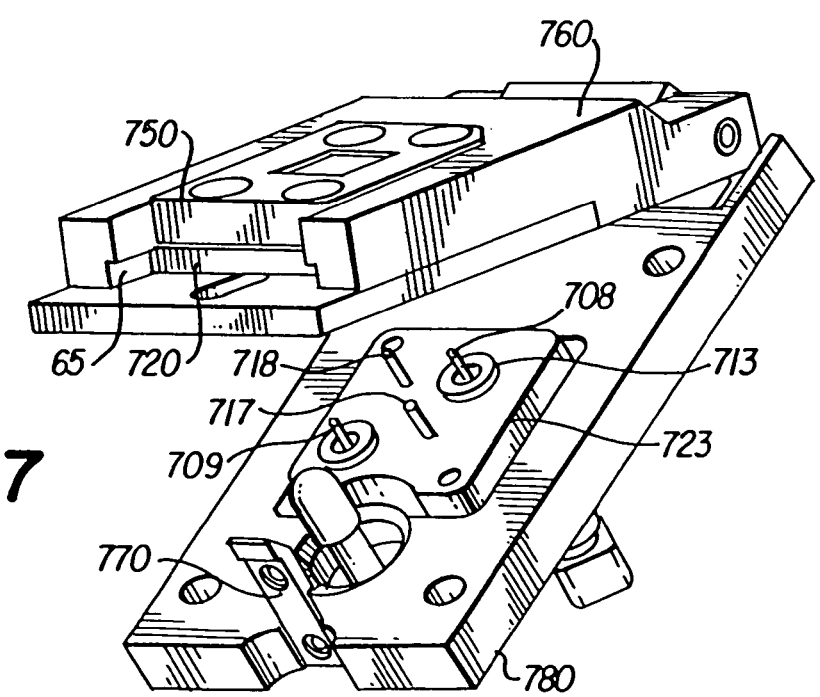
FIG. 7 shows another embodiment of an FTC cartridge according to the present invention.

The system controller 250 can include a microprocessor or computer that is programmed with software, such as Lab-View (available from National Instruments, Austin, Tex.) that can control one or more of the systems described above. With the control system of the present invention, flow rates, buffer selection, temperature, and timing for one or more FTCs can be controlled independently. These components will be described in detail below FIG. 3 shows an exploded detailed view of the FTC cartridge 300 that can be used with the system of FIG. 2. The FTC cartridge 300 can include a base or bottom piece 310, a chip holder 320, an FTC 330, sealing seals or seals 331, 333, 334, a window 340, and a cover 350. The base, 310, chip holder 320, and/or cover 350 can be made from a wide variety of solid materials, such as metals, semi-metals, composites, plastics, and injection-molded materials. In the embodiment shown in FIG. 3, the structural components of the FTC cartridge 300, namely the base 310, chip holder 320, and cover 350, can be constructed from anodized aluminum. Alternatively, these components can also be formed as a single construction, such as by conventional injection molding, as will be apparent to one of skill in the art given the present description. FIG. 7 discloses an embodiment of the FTC cartridge formed as a single piece.

The base 310 can include passages for a flow control system (described in detail below in conjunction with the description of FIG. 7), such as a two pin/septa system (via an inlet 308 and an outlet 309). The flow delivery system, such as the pin/septa system, allows flow control of the test fluid mixture used in an assay. The base 310 can include additional pin/septa as needed. The base 310 can further include an alignment indicia or tool, such as a bevel 312 to ensure that the FTC cartridge 315 is properly assembled with a fluid control system, such as the fluidics station of FIG. 11, thereby reducing user assembly error. The base 310 can further include a recess 311, which is used to hold or contain a thermal fluid. The thermal fluid can be delivered to the FTC cartridge 300 via a fluid delivery mechanism, such as the pin delivery mechanism shown in FIG. 7. The thermal fluid is ultimately used to provide for the temperature control of the FTC. In particular, the thermal fluid is used to control the temperature of the test fluid mixture (also referred to as target solution) around the FTC, while the assay is running and while the test fluid mixture is flowing through the FTC. Example thermal fluids include, but are not limited to, water and aqueous solutions of ethylene glycol and the like.

An insert 313, such as a thermal seal, can be used to further control and localize the thermal fluid delivered to the FTC cartridge 300. The insert 313 can be formed from compressible materials such as CHR silicone, Volara, Poron, Minicell EPOM and the like. Alternatively, rubber, Viton, silicone, Buna-N, Neoprene rubber, and the like, can also be used. Moreover, the base 310 can be designed to include a set of walls or boundaries, i.e., a recess forming a chamber 311, to localize the containment of thermal fluid. The insert 313 is designed to isolate the thermal fluid from contact with (and subsequent contamination of) the test fluid mixture delivered to the FTC cartridge 300. The insert 313 defines a thermal chamber 314 formed at the bottom side of chip holder 320. That is, the insert 313 forms a closed thermal chamber 314 that is isolated from the test (or process) fluid loop. The thermal fluid chamber 314 can be coupled to a temperature controller, such as environmental control system 230 shown in FIG. 2. For example, an external temperature controller, such as a conventional fluid bath and pump system, can deliver temperature controlled fluid to the thermal chamber 314 to heat or cool the test fluid chamber (discussed below), to facilitate temperature controlled hybridizations. Alternatively, the thermal chamber 314 can be substituted with a closed and controlled environmental chamber in which the fluid lines and the FTC cartridge are enclosed. Alternatively, the thermal chamber 314 can be designed to house an alternative temperature-controlling device, such as a thermo-electric heating/cooling device or a Peltier heating/cooling device, thereby eliminating the need for a thermal fluid delivery system. The alternative temperature-controlling element can be integrated into the FTC cartridge 300 or into a stage that accepts the FTC cartridge 300.

The base 310 can further include one or more additional recesses 318 that are designed to accurately position septa 317, through which the pins/needles (708, 709) that deliver the test fluid mixture pierces. Similarly, additional septa 315 can be used to accept pins/needles (717, 718) that deliver the thermal fluid. See FIG. 7.

The base 310 can further include mounting holes, such as hole 319, which can be adopted to secure fasteners, such as screws or clips, that secure the cover 350 to the base 310. Alternatively, the FTC cartridge 300 can be designed as a single construction (FIG. 7), thus obviating the need for such fasteners and mounting holes.

The chip holder 320 is designed to hold a flow-through device, such as an FTC 330, during an assay. The FTC 330 is schematically illustrated as a square structure, but can be rectangle, circular, or have other polygonal shape. The chip holder 320 can provide other functions, such as housing the thermal chamber 314 and providing a test fluid (or process) chamber. The chip holder 320 is designed to provide a uniform flow of test fluid through the FTC 330. Seals can be used with the chip holder 320 minimizes leakage of thermal and test fluids. Also, the chip holder 320 can support the observation window 340, as well as minimize scattering effects that can cause spurious optical signals during an assay. One method of reducing potential scattering effects is to coat the chip holder (as well as the other components of the FTC cartridge) with a flat black, low light reflecting, reduced scatter coating. This low light scatter coating helps reduce the amount of background light (signal) present during imaging.

Figure 10:
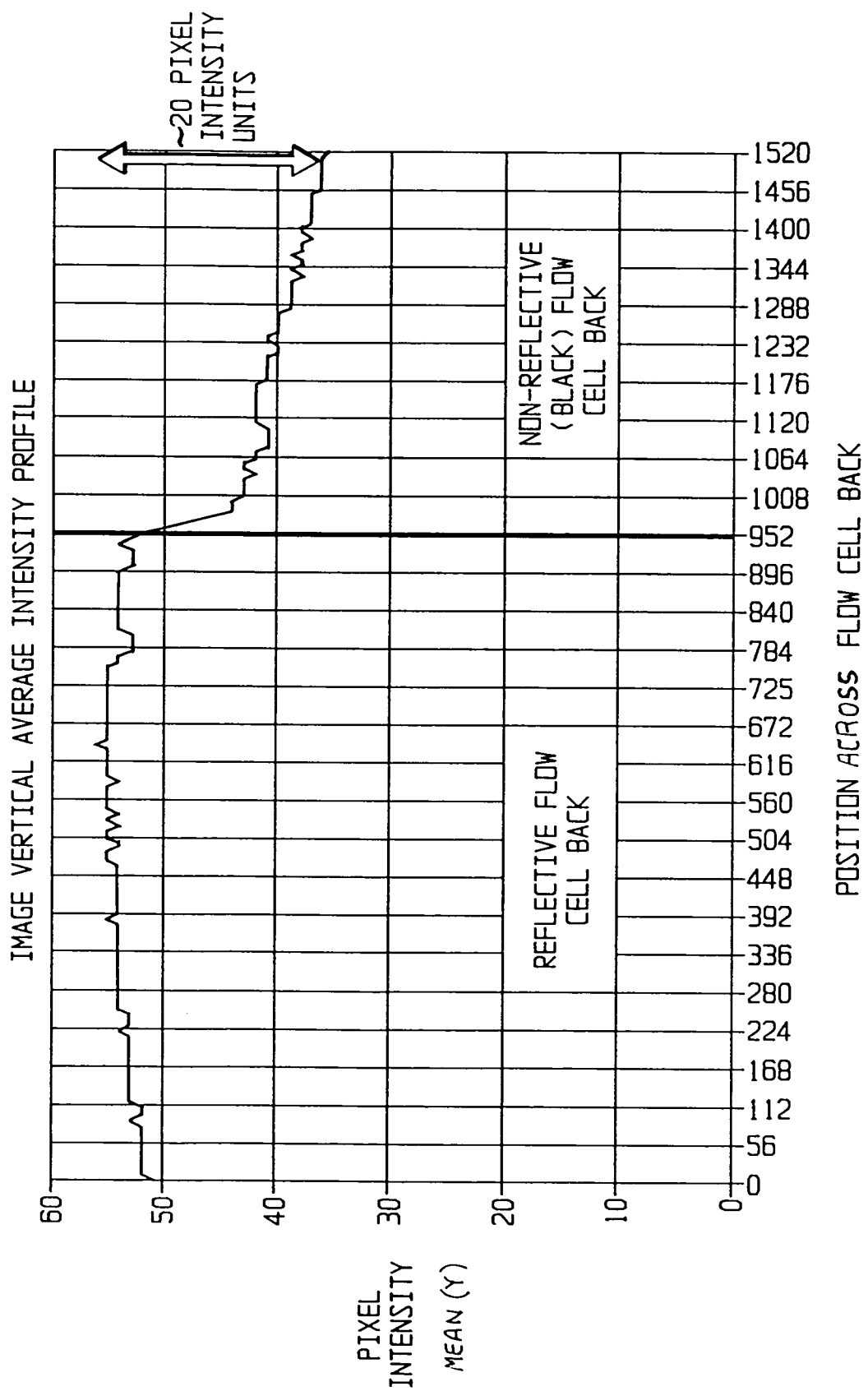
FIG. 10 shows a chart illustrating the effects of reflective and non-reflective flow cell surfaces.

Indeed, a test performed comparing the relative background noise for a reflective coated chip holder (polished aluminum) versus a non-reflective coated chip holder (anodized aluminum) confirms the scattered light reduction. In particular, FIG. 10 shows the effects of reflective and non-reflective flow cell surfaces on image background pixel intensity. The left side of the graph (having a reflective flow cell back surface) shows a much higher background signal noise (by about 20 arbitrary pixel units) than the right side of the graph, which corresponds to the background signal of the flow cell having a black/anodized coated back surface.

Figure 4A:
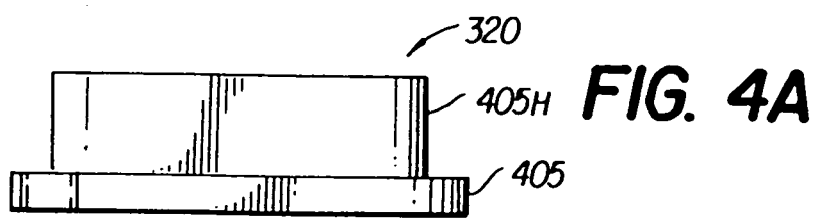
Figure 4B:
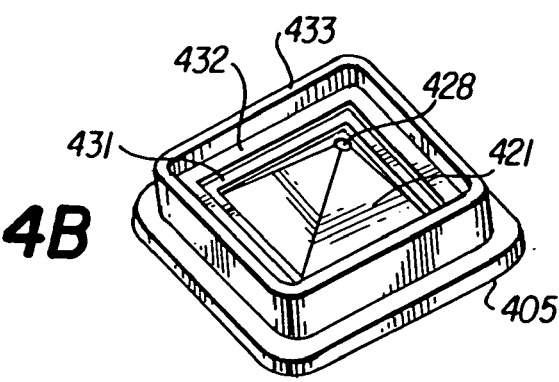

Detailed views of the chip holder 320 are shown in FIGS. 4A-4G. FIG. 4A shows the side view of the chip holder 320. The chip holder 320 comprises a body with an outer ridge 405 and a substantially hollow member 405H extending upwardly from the outer ridge 405. The ridge 405 is contoured to snuggly seat into the recess 311 formed in the base 310. A bevel in one of the corners can be used to ensure proper alignment within the base 310. Again, the shape of the chip holder 320 and the outer ridge 405 can have different shapes, depending on the contours of the base 310. The chip holder 320 can be manufactured from anodized aluminum. The anodized or black coating can be used to reduce light scattering effects produced during optical-based assays. Alternatively, the chip holder 320 can be made from plastics, metals, semimetals, silicon-based materials, or injection-molded plastics. Further, the chip holder 320 and the base 310 can be formed as a single unit, and even monolithically.

Figure 4C:
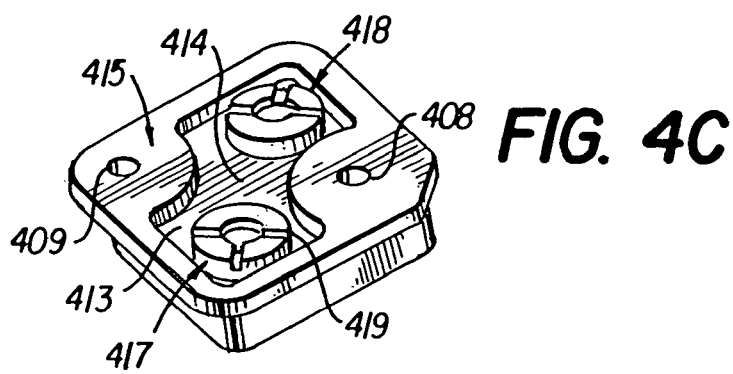

Referring to FIG. 4C, the underside of the chip holder 320 can include a recess 414, which defines an upper portion of the thermal chamber 213. Thus, the upper and lower chambers 414 and 314 both define the thermal fluid chamber 213 (in FIG. 2 or 451 in FIG. 5C), which is used to contain thermal fluid for temperature control of the test fluid mixture. The correspondence in shape of chambers 414 and 314 is important to ensure that the thermal fluid is confined and not mix with the test fluid mixture. In addition, the depth of the recessed portion 414 (which corresponds to the distance between the upper surface 413 of the thermal fluid chamber and the flow surface 421, discussed below) can be optimized to ensure efficient heat transfer between the thermal fluid chamber 213 and the test fluid chamber 211. The efficient heat transfer properties of the FTC cartridge 300 of the present invention facilitate well-controlled assays that determine the effects of temperature changes on hybridizations.

Also included within the recessed portion 414 are ports 417, 418 for introducing and draining the thermal fluid into the test fluid chamber 211. These ports 417, 418 can be positioned to correspond to the location of the thermal fluid pin/septa in the base 310. The ports 417, 418 can further include one or more slots or channels 419, which are used to distribute the thermal fluid flow and help to provide a uniform temperature distribution within the thermal chamber 213. As shown in FIG. 4C, the ports 417, 418 each include three fluid flow slots 419. The bottom side 415 of chip holder 320 further includes an entrance guide hole 408 and an exit guide hole 409, which correspond in location to the inlet 308 and the outlet 309 discussed above. Thus, a test fluid mixture will enter into the test fluid chamber 211 via the inlet 308 and entrance guide 408, and exit the FTC cartridge via the exit guide hole 409 and the outlet 309.

Figure 4D:
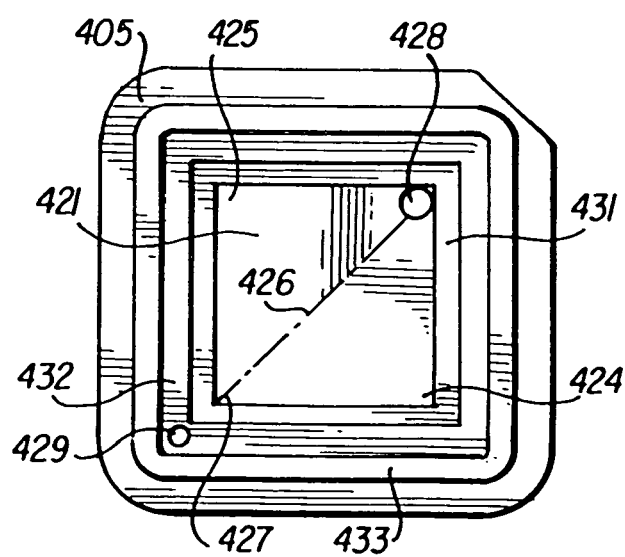
Figure 5A:
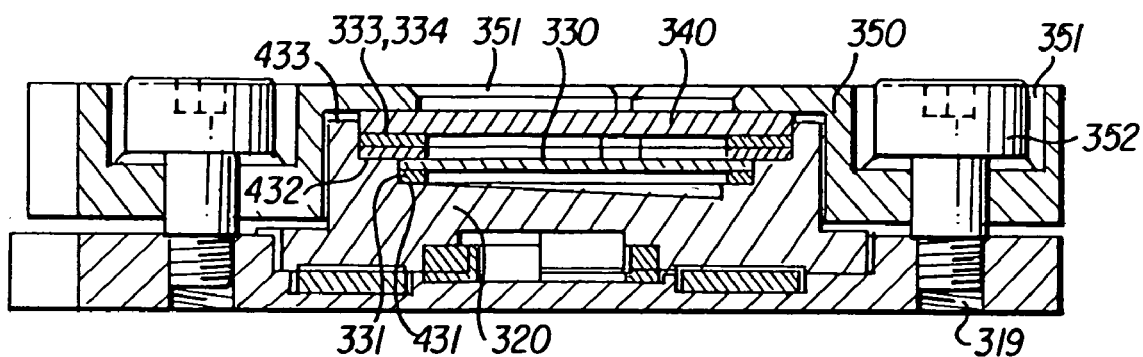
FIGS. 5A-5C show detailed cross-sectional views of the assembled FTC cartridge of FIG. 3.
Figure 5B:
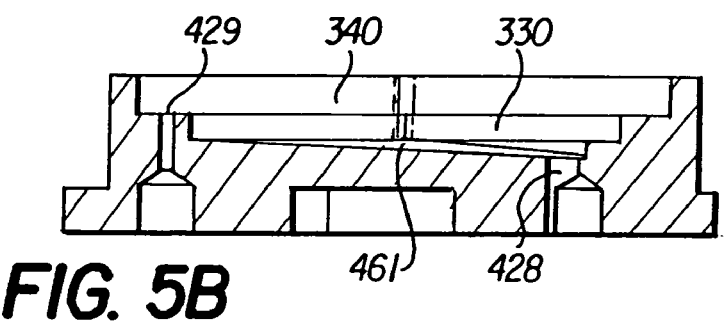
Figure 5C:
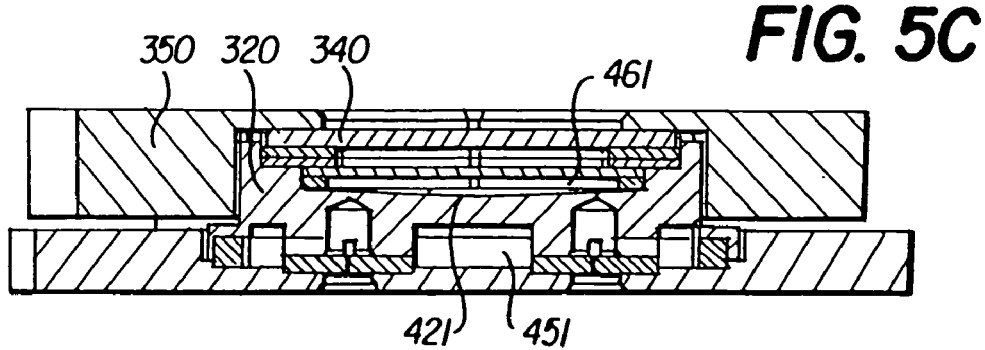

Referring now to FIGS. 4B and 4D-4G, another unique feature of the chip holder 320 lies with the flow surface 421, which in turn defines the shape of the test (or process) fluid chamber or the flow cell (identified in FIGS. 5B and 5C as chamber 461). The test fluid chamber 461 is defined, in part, by the flow surface 421 and the bottom side or bottom surface of the FTC 330. The surface 421 can include a single entrance hole 428 for introducing a test fluid mixture into the test fluid chamber 461. The single entrance hole 428 can be provided near one corner of the chip holder 320, such as illustrated in FIG. 4D. The present inventors have found that a single entrance hole located in a corner region is advantageous over other entrance port schemes (e.g., ports from the perimeter of the FTC where fluid flows parallel and perpendicular to the sides of the FTC). Alternatively, multiple inlets and outlets from the chip holder (as well as from other components of the FTC cartridge can also be employed to distribute the fluid more uniformly across the FTC 330.

According to an aspect of the present invention, the flow surface 421 is deliberately angled so that it has a spade—or shovel—like shape that changes in elevation relative from one corner to the opposite corner. Referring to FIGS. 4D, 4E, and 4G, the lower elevational end is adjacent to the entrance hole 428 and higher elevational ends are located at an opposite corner portion 427 and corner portions 424 and 425. A first slope along the diagonal ($\alpha_1$) is shown in FIG. 4E, where the relative elevation of the flow surface 421 varies from the entrance hole 428 to the opposite corner portion 427. The slope angle $\alpha_1$ can range from about 1 to about 20°, more preferably between about 1° to about 4°. A slope angle of about 2.55° is most preferred. A second slope angle ($\alpha_2$) is measured from entrance hole 428 to corner portions 424 or 425. FIG. 4G shows the second slope angle C as measured from the entrance port 428 to corner portion 424. The second slope angle can range from about 1° to about 20°, more preferably between about 1° to about 5°. A slope angle $\alpha_2$ of about 3.7° is most preferred. But these slope angles can be varied, depending on various factors, such as fluid viscosity, fluid force, and the degree of uniformity of flow required for a particular assay. In addition, the slope of the flow surface 421 can be further varied depending on the number of test fluid entrance points used and the uniformity of flow required for an assay.

The spade or shovel-like shape of the flow surface 421 is further illustrated in FIG. 4F, which shows a side view of the flow surface 421 from the perspective of the entrance hole 428. As shown in FIG. 4F, the flow surface 421 includes a trench (i.e., V-shaped) that is defined by its lowest and highest relative points along line 426 (FIG. 4D) at the opposite corners, at the corner portion 427, and the opposite sides or corner portions 424 and 425 having the highest point relative to the trench along the line 426. In the rectangular/square configuration shown in FIGS. 4A-4G, the length of trench line 426 is along the diagonal of flow surface 421. Thus, the trench angle can vary along the length of the trench line 426. As shown in FIG. 4F, the trench angle β is measured at a midpoint of line 426. In this regard, the angle of the trench can be between about 0.5° to about 12°, or about 1° to about 5°. A trench angle β of about 2.6° is most preferred. Of course, the trench angle β of the flow surface 421 can be varied depending on the number of test fluid entrance points used and by the degree of uniform flow required for a particular assay. The chip holder 320 also can employ a bowl-back design for its test fluid chamber, as described in more detail below.

The spade-like shape of the flow surface 421 is used to equalize fluid pressure moving across the two-dimensional geometric area of the FTC. As fluid flows from the source of fluid pressure (i.e., entrance 428), the slope maintains the backpressure at the base of the chip holder. This shape forces fluid into a constantly decreasing volume beneath the FTC as it moves from the fluid pressure source.

Figure 8:
FIG. 8 shows an FTC image illustrating non-uniform fluid flow using a flat-back flow cell.
Figure 9:
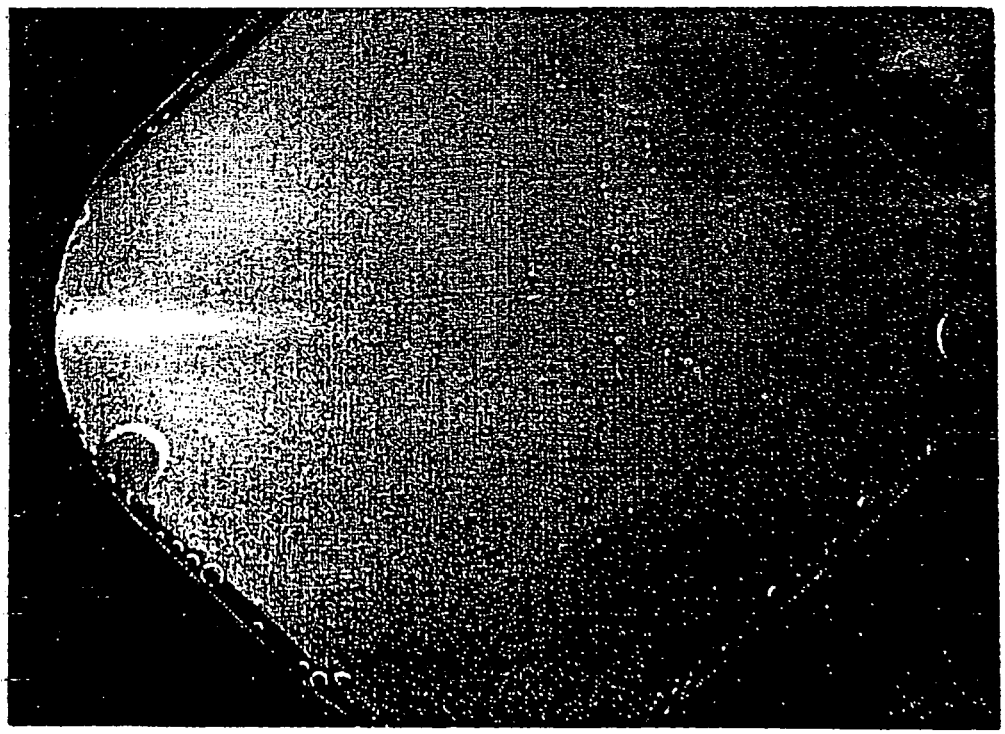
FIG. 9 shows an FTC image illustrating substantially uniform fluid flow using a flow cell according to the present invention.

The importance of the uniformity of flow can be further illustrated in relation to experiments performed by the inventors, the results of which are shown in FIGS. 8 and 9, as well as discussed in Experiment 4 below. FIG. 8 shows a fluorescent microscope image of flow in a multi-port, flat-back flow cell, with the flow rate being approximately 0.2 milliliters per minute (ml/min.). This image shows multiple bright and dark image regions, indicating different flow rates in different areas of the FTC being images. FIG. 9, on the other hand, shows a fluorescent microscope image of flow in a single-port, flow cell having a spade-like surface, similar to the embodiment described above. Both images were taken after an identical period of elapsed time. The image shown in FIG. 9 shows a much more uniform flow through the FTC, as indicated by the substantially uniform image intensity across the FTC. The results of a comparison between the two figures show that the test fluid chamber having a spade-like configuration, such as a V-shaped cross-sectional profile, greatly enhances the uniformity of flow.

Referring back to FIGS. 4B and 4D, a series of shelves or lips 431, 432 can be designed within the substantially hollow member 405H to support the FTC 330, the observation window 340, and/or one or more seals. This arrangement allows use of seals to minimize leakage of a test (i.e., process) fluid mixture. For example, in FIGS. 4D and 5A, a lower shelf 431 extends inwardly from the member 405H and around the periphery of the flow surface 421. A lower seal 331 (FIG. 5) is sandwiched between the shelf 431 and the lower side of the FTC 330. The shelf 431 allows the lower seal 331 to be disposed within the chip holder 320 in a level manner, as shown in more detail in FIG. 5A, to allow the FTC 330 to be at level. The design of the shelf 431 can vary depending on the type of seal used.

Figure 6A:
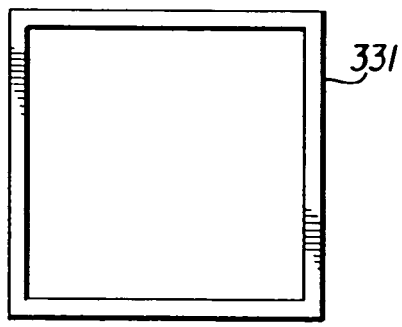
FIGS. 6A-6D show alternative embodiments of seals usable in the FTC cartridge of FIG. 3.
Figure 6B:
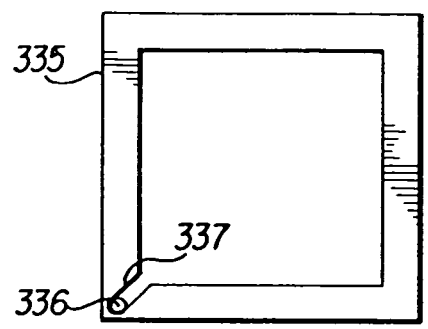

As mentioned, the FTC 330 is placed over the lower seal 331, which provides a cushioned support for the FTC and helps reduce leakage around the sides of the FTC, thus ensuring that test fluid will flow from the test fluid chamber through the FTC. As shown in FIGS. 4D and 5A, the chip holder also includes an upper shelf 432 extending inwardly from the member 405H. The upper shelf 432 is designed to allow a snug placement of an upper seal or seals 333, 334, on top of the FTC 330. In addition, the upper shelf 432 further includes an exit hole 429, which directs test (or process) fluid that has passed through the FTC to the exit guide hole 409 and out of the FTC cartridge 300. The perimeter of the upper shelf 432 is designed to conform to the shape of the upper seal(s) to prevent leakage of the test (or process) fluid around the FTC 330. The height of the upper shelf 432 can be designed such that the lower side of the upper seal 334 contacts the perimeter region of the FTC 300. The chip holder 320 can further include an upper ridge 433, which is designed to conform to the shape of the observation window that is disposed on an upper surface of the upper seal(s) 333, 334, which can be a single seal, as shown in FIG. 6B.

The single upper seal 335 further includes a hole 336 and a slot or channel 337. The location of hole 336 corresponds to the location of the exit hole 429 (FIG. 4D), which directs test (or process) fluid that has passed through the FTC to the exit guide hole 409 and out of the FTC cartridge. The slot 337 in turn further directs the flow of test fluid that emerges from the microchannels of the FTC into the hole 336. In addition, the upper seal can be designed to have inner perimeter rounded corners to help enhance the wetting properties of the FTC cartridge. The lower seal 331 and upper seal 335 are designed to maximize the active area of the FTC (i.e., the area where flow is allowed to pass through the microchannels of the FTC). The upper and lower seals can cover a 1-millimeter wide perimeter on the FTC. Other seal designs for directing fluid flow will be apparent to those of skill in the art given the present description.

Figure 6C:
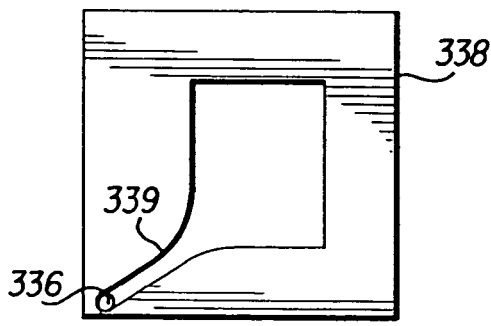

An alternative seal 338 is shown in FIG. 6C. The seal 338 is designed to provide for a smaller active area for the FTC. This design allows an experimenter to localize or "focus" a test fluid, such as a target solution, on a particular region of the FTC. The seal 338 can further include a hole 336 and a fluid flow channel 339, similar to those of FIG. 6B.

Figure 6D:
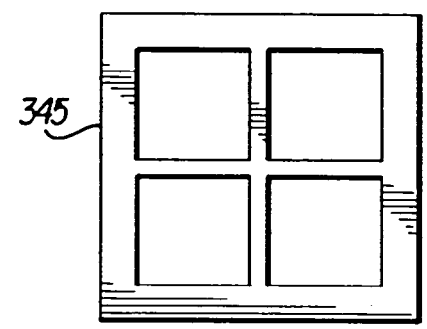

Another alternative upper seal 345 (FIG. 6D) has more than one opening, thus providing for multiple active areas. Test fluid can then only flow through particular regions of the FTC. A bottom seal (not shown) of similar design can be employed, thus creating a series of tunnels, to further direct fluid flow through only particular regions of the FTC. In another alternative embodiment, the seals 331 and 335 can be formed as a single seal that surrounds a perimeter region of the FTC. For example, a single shrink-wrapped seal can be placed around the perimeter of the FTC then treated to form fit upper and lower portions around the perimeter of the FTC.

The seals reduce leakage of the test fluid flowing through the FTC 330. In addition, the seals further ensure proper test fluid flow through the FTC and back into the fluid delivery mechanism, as opposed to an alternative path around the perimeter of the FTC. Further, the seals reduce the number of metal/glass contact points that could potentially damage the FTC. The upper and lower seals of the present invention can be formed from any material commonly used in sealing applications. For example, the seals can be formed from rubber, Viton, silicone, Buna-N, Neoprene rubber, and the like. In a preferred embodiment, the upper and lower seals are Viton rubber. Viton is advantageous in that it is non-fluorescent, it maintains its shape over many uses, and it does not react with or promote analyte binding to its surface.

Referring back to FIG. 3, the FTC 330 can include any flow through device that includes a substrate containing a first and second surface, where the channels extend through the substrate from the first to the second surface. Suitable substrate materials include microchannel or nanochannel glass and porous silicon, which can be produced using known microfabrication techniques.

The in situ observation window 340 can be designed to be disposed on the upper seal 334 and snugly fit inside the upper ridge 433 of the chip holder 320. See FIG. 5A. The window 340 can be formed from a variety of materials including, but not limited to, glass (doped and undoped), quartz, or any other transparent material that does not interfere with the signal of interest emanating from the FTC. In addition, window 340 can be made from wavelength-specific filter glass that selectively transmits incident and exiting light, such as at the emission and excitation wavelengths of a fluorophore being used in a FTC experiment. In a preferred embodiment, window 340 includes borosilicate glass, which is advantageous because it costs low and minimally interferes with the fluorescence microscopy used to image FTCs. The window 340 allows visualization of a FTC reaction in real time under a fluorescence microscope, for those experiments where an analyte to be detected is pre-labeled with a light emitting reporter molecule.

The window 340 can have a thickness of about 1 mm or less and can be disposed at a distance of about 1 mm from the top of the FTC. The inventors have discovered that a window thicker than 1 mm tend to absorb and scatter more light, thereby reducing light collection efficiency. Accordingly, the thickness of the glass can be selected according to the type of glass used and the light collection efficiency desired. In alternative embodiments, the chip holder can be designed such that the distance between the bottom surface of the window and the top surface of the FTC is minimized to reduce potential scattering, while taking into account fluid flow considerations.

As shown in FIGS. 5A and 5C, the window 340 can be held in place by a cover 350 to provide a uniform cartridge compression of the sealing seals around the perimeter of the FTC. As with the other components of the FTC cartridge 300, the cover 350 can be made of any of the structural materials mentioned above. In a preferred embodiment, the cover 350 is constructed of anodized aluminum.

As shown in FIGS. 3 and 5A, the cover plate 350 includes an opening 351 that allows the passage of light to and from the FTC. Recessed holes, such as a hole 355, are provided to guide the compression/fastening devices, such as a screw 352 and a washer 353, to their proper locations to fasten the cover 350 onto the base 310. For example, four shoulder screws and corresponding spring washers can be used to uniformly compress the FTC cartridge. More specifically, shoulder screws can be used to set the distance between the top and bottom cartridge components. The spring washers compress the top and bottom cartridge pieces with a controlled force equal to the additive force of all four springs. This significantly enhances cartridge loading reproducibility and control over designs using fewer screws or fasteners.

In an alternative embodiment shown in FIG. 7, the aluminum FTC cartridge material can be substituted with injection molded parts that snap together to form a uniform and reproducible seal. For example, an FTC cartridge 720 (having a FTC, a thermal chamber, a test fluid chamber, and a sealing subsystem, similar to those described previously) can be integrally formed with a top cover 750 that is either formed into or placed in cartridge casing 760, for example by sliding along a track 765. A latch or snap fitting 770 can be disposed on the cartridge casing or on the fluid delivery stage 780 to which the FTC cartridge interfaces to provide a sealing of the fluid delivery pins/needles with the FTC cartridge.

Figure 17A:
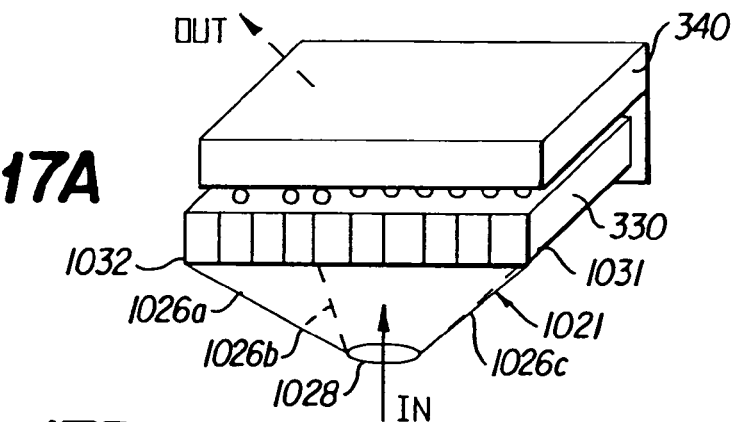
FIG. 17A shows an alternative flow surface of the test fluid chamber.
Figure 18A:
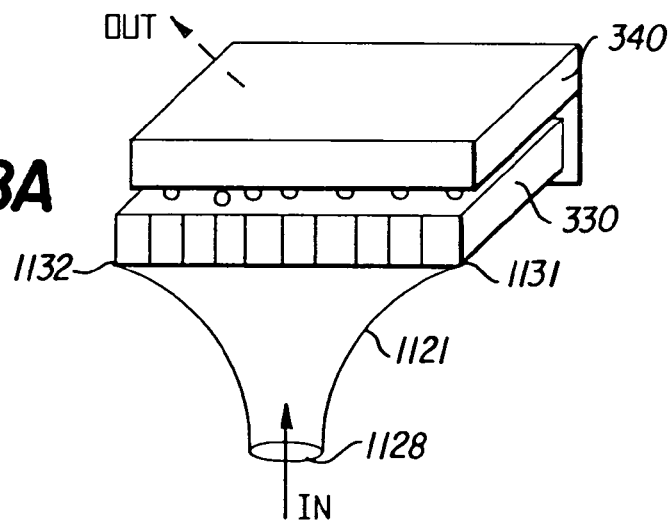
FIG. 18A shows another alternative flow surface of the FTC test fluid chamber.

FIGS. 17A and 18A show alternative embodiments of the flow surface of the FTC test fluid chamber. Other alternative structures will be apparent to those of skill in the art given the present description.

FIG. 17A shows a flow surface 1021, the FTC 330, and the window 340. The FTC 330 and the window 340 have been described above. The flow surface 1021 has an entrance port 1028 located at its central region. The flow surface 1021 slopes upwardly and outwardly (as shown in FIG. 17A) toward the periphery of the FTC 330, such as perimeter edges 1031 and 1032. As shown in FIG. 17A, the flow surface 1021 includes multiple trenches (i.e., V-shaped channels) 1026a, 1026b, and 1026c, to form a pyramid-configuration. The slope of the trenches (as measured from the entrance port to the perimeter) can have any practical slope, from about 0.5° to about 12°, desirably between about 1° to about 5°. Of course, the number of trenches, entrance ports, and the slope of the trenches of the flow surface 1021 can be varied depending on the degree of uniform flow required for a particular assay.

Figure 17B:
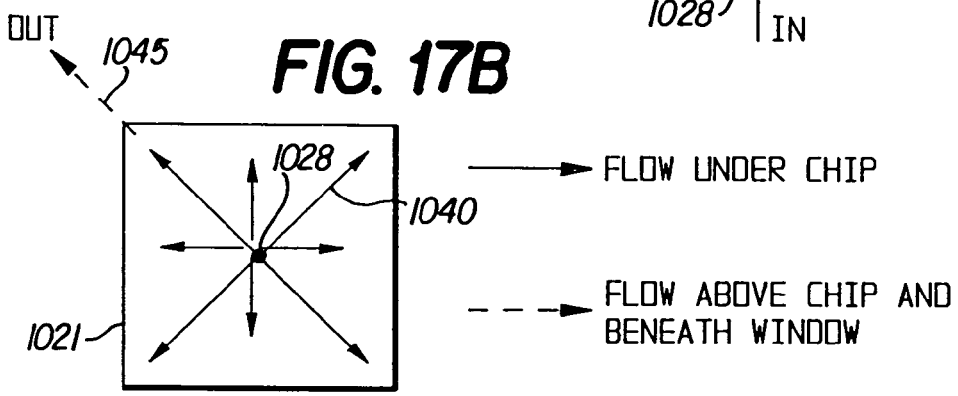
FIG. 17B schematically illustrates a fluid flow diagram of the flow surface of FIG. 17A.

The flow direction of the flow surface 1021 is shown in FIG. 17B. The solid arrows 1040 illustrates test fluid flow underneath the FTC. In this embodiment, four diagonally configured sloped trenches (i.e., 1026a, et seq.) can be utilized to produce the type of test fluid flow shown in FIG. 17B. The dashed arrow represents the test fluid flow above the FTC and beneath the window. For example, this fluid flow above FTC 330 can be produced utilizing a single upper seal, such as the seal 335 shown above in FIG. 6B, which includes the hole 336 and the slot or channel 337 to direct fluid flow away from the FTC.

The embodiment of FIG. 18A also has a flow surface 1121 with an entrance port 1128 located centrally of the flow surface 1021. The flow surface 1121 curves upward and outwardly toward the periphery of the FTC 330, such as perimeter edges 1131 and 1132, forming a funnel configuration., which is devoid of trench like structures. Of course, the curvature of the flow surface 1121 can be varied depending on the degree of uniform flow required for a particular assay.

Figure 18B:
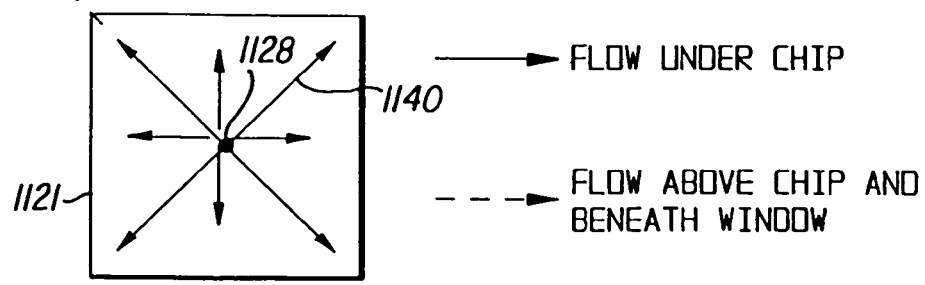
FIG. 18B schematically illustrates a fluid flow diagram of the surface of FIG. 18A.

The flow-direction of flow surface 1121 is shown in FIG. 18B. The solid arrows 1140 illustrates test fluid flow underneath the FTC. In this embodiment, the flow surface provides a substantially uniform flow distribution toward the perimeter. The dashed arrow represents the test fluid flow above the FTC and beneath the window. For example, this fluid flow above FTC 330 also can be produced utilizing a single upper seal, such as the seal 335 shown above in FIG. 6B, which includes the hole 336 and the slot or channel 337 to direct fluid flow away from the FTC. A seal with multiple exit channels can also be utilized as would be apparent to one of skill in the art given the present description.

Referring now to FIG. 7, a test fluid mixture can be delivered to the FTC via a test fluid delivery mechanism or assembly 723. The assembly 723 can include one or more fluid delivery pins/needles that are coupled to a fluidics station, such as the one illustrated in FIG. 11. The assembly includes an inlet pin 708 and an outlet pin 709 to provide a closed loop fluid circulation. Optionally, vacuum seals, such as a vacuum seal 713 or septa, can be used to prevent leakage and contamination of the test fluid mixture. In addition, if thermal fluid is being delivered to the thermal fluid chamber 213, separate inlet and outlet pins 717 and 718 can be used. In addition, septa for each of the pins can be provided in the FTC cartridge, as discussed previously. Alternatively, a single septum can be used as opposed to four separate septa.

A pin/septa-based fluid delivery system can be used for the interface between the fluidics station and the FTC cartridge because these components are re-useable. They allow a user to remove and replace cartridges from the fluid delivery system without introducing air bubbles. Factors to consider in the use of specific pin/septa systems include (1) if the pin is too small, there can be an undesirable coring of the septa and (2) if the pin is too large, the risk of leakage increases. For example, pins having holes to the side (see e.g., FIG. 7) can be used to deliver the test fluid. Such a pin design can reduce the probability of orifice occlusion. Septa materials such as silicone-based materials, PTFE, Viton, and the like can be used.

Figure 11:
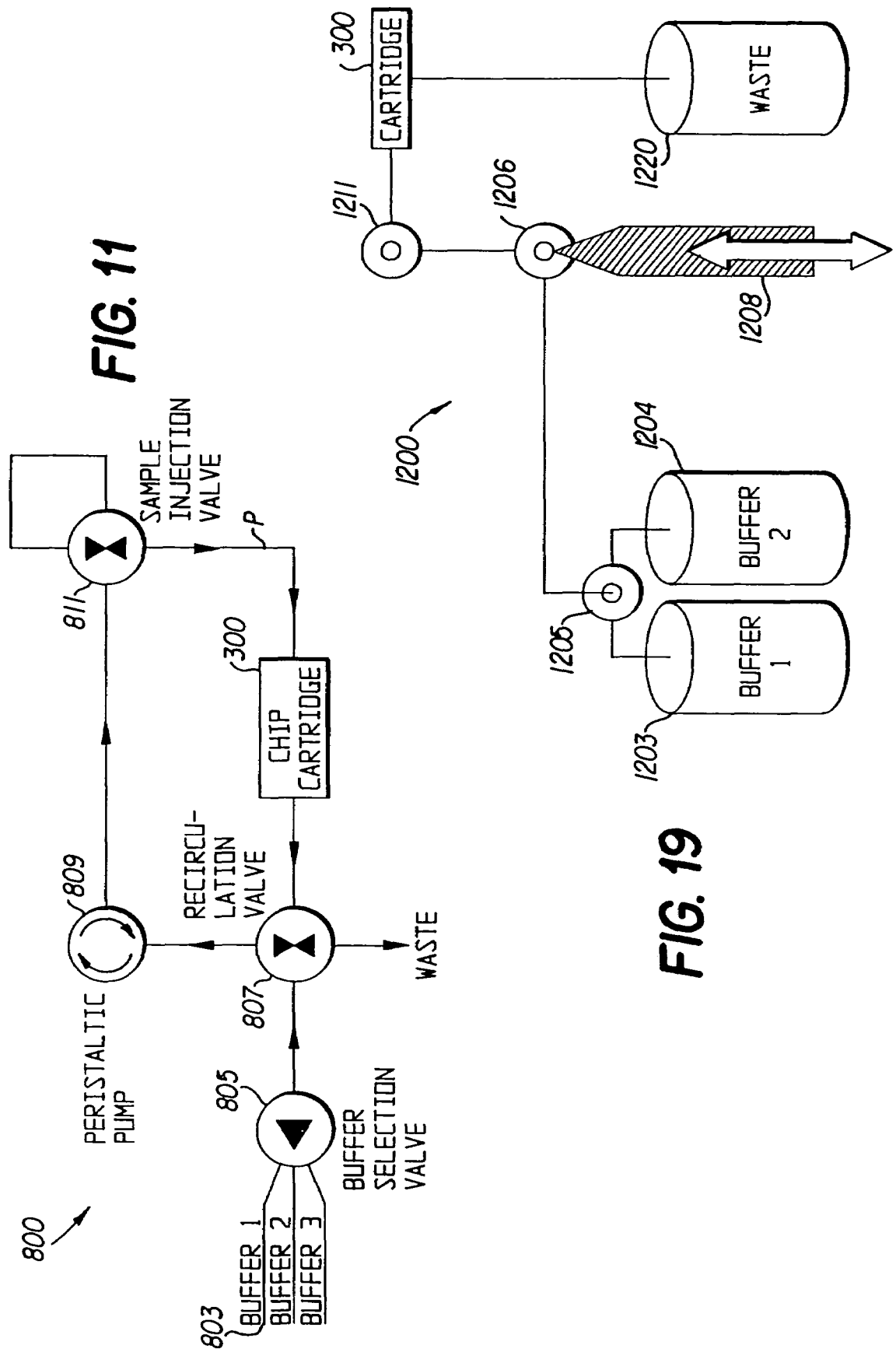
FIG. 11 shows a schematic view of a fluidics station for delivery of fluid to the FTC cartridge of FIG. 3.

According to another aspect of the present invention, the FTC cartridge 300 can be in fluid communication with a fluidics station that facilitates target re-circulation through the FTC. FIG. 11 shows an example fluidics station 800 that can be used with the FTC cartridge 300 according to the present invention. In this embodiment, the fluidics station 800 can include three valves: a buffer selection valve 805, a re-circulation control valve 807, and a sample injection valve 811. The fluidics station 800 can further includes a peristaltic pump 809, and an FTC cartridge, such as the FTC cartridge 300 shown in FIGS. 3-5. Fluids can communicate through these elements in a circular loop through a fluid path P.

In operation of the fluidics station 800, the re-circulation valve 807 switches between an open circuit mode or position and a closed circuit mode or position. In the open circuit mode, the valve 807 directs buffer fluids from the buffer reservoirs 803 into the fluid path P, into the pump 809, into the FTC cartridge 300, and back to the valve 807, which directs flow to waste. The open circuit mode can be used to wash the FTC cartridge, as well as for pre- and post-preparation of a hybridization process. During the open circuit mode, a test sample fluid is loaded into the sample injection valve 811, which is isolated from communication with the open circuit of flow path. In order to begin a hybridization (after the fluid line P and the cartridge 300 have been filled with fluid, e.g., buffers), the valve 807 can be switched to the closed circuit mode. In the closed circuit mode, the valve 807 closes communication with the buffer reservoirs 803 and the waste, so that the buffer flows in a closed loop through the pump 809, the FTC cartridge 300, and back to the pump 809. Once a closed loop is achieved, the sample injection valve 811 (having been previously loaded with a test sample) is opened to fluid communication from the pump 809 and to the cartridge 300 such that fluid flow from the pump 809 is diverted through the sample injection valve for the duration of the hybridization, and the reaction proceeds while the pump re-circulates the test sample through the closed circuit for a designated period. The 809 can be used because it is cost effective, it can be used as an external, non-invasive pumping system, it can pump fluid in a closed loop, and it can be easily configured to a large range of fluid flow rates. Alternatively, a cartridge-internal pump, such as a miniature peristaltic pump or an electrode-based pumping device can be used.

The fluidics station of the present invention in conjunction with the FTC cartridge offers an advantage over conventional assays in that the fluidics station and the FTC cartridge facilitate multiple-pass target experiments. As the inventors have determined, a single pass of a target through an FTC can have limited sensitivity, thus requiring some form of amplification of the signal to determine low abundance targets. Sensitivity can be enhanced or increased by passing the target (contained in the test (or process) fluid mixture) through the FTC more than one time.

In operation, a test fluid is delivered to the FTC cartridge by a fluid delivery system, such as the fluidics station 800. The test fluid enters an entrance port, such as the inlet 428 shown in FIG. 5B. The test fluid then flows into a test fluid delivery chamber that is designed to provide a substantially uniform flow through the FTC (e.g., chamber 461 shown in FIGS. 5B and 5C). The fluid then passes up through the microchannels of the FTC. The seals prevent the fluid from flowing in other areas. After passing through the FTC, test fluid is directed to an outlet, such as the outlet hole 429 shown in FIG. 5B. The test fluid returns to the fluidics station where it can be re-circulated or disposed of as waste. Thus, the FTC cartridge and the fluidics station according to the present invention can provide a system that directs the flow of test (or process) fluid through a FTC in a controllable manner.

In addition, the fluidics station according to the embodiment of the present invention shown in FIG. 11 can include a system for the delivering and temperature controlling of a thermal fluid to the FTC cartridge. For example, the fluidics station 800 further include a temperature control unit, such as a conventional water chiller unit or an immersion circulator, for controlling the temperature of the thermal fluid delivered to the FTC cartridge.

Alternatively, a fluidics station 1200 can also provide a reverse flow. FIG. 19 shows such a fluidics station 1200, which can use a syringe pump 1208 to inject or withdraw a test sample through the FTC. The fluidics station 1200 includes a sample injection valve 1211, a FTC cartridge 300, such as the ones described above, an aspirate/dispense valve 1206, the syringe pump 1208, a buffer selection valve 1205, and buffer reservoirs 1203 and 1204 (additional buffer reservoirs can also be included). Optionally, a waste solution reservoir 1220 can also be included having a lengthy conduit in communication with the FTC cartridge 300. Other arrangements of these components than that is shown in FIG. 19 would be apparent to those of skill in the art given the present description.

For example, the fluidics station 1200 can operate as follows. In a pre-hybridization routine, the syringe pump 1208 aspirates buffer from the buffer source 1203, 1204 and dispenses buffer into the cartridge 300 and out to the waste 1220. During this routine, a test sample can be loaded into the sample injection valve 1211, which can be similar to or the same as same as sample injection valve 811 shown in FIG. 11.

In a hybridization routine, the aspirate/dispense valve 1206 (which can be a two position valve) is placed in a cartridge/waste position. Also, the sample injection valve 1211 is opened to communicate with the syringe pump 1208 so that the syringe pump 1208 can position a slug of the test sample inside the cartridge 300 containing the FTC. After positioning, the syringe pump 1208 can oscillate the test sample back and forth across the FTC for a designated period of time. The amount of test fluid that flows into and out of FTC cartridge 300 can be a very small volume for the hybridization routine. For example, in a forward flow direction, the syringe pump 1208 injects test fluid into cartridge 300. In a reverse flow direction, syringe pump 1208 withdraws test fluid from the cartridge 300, where excess test fluid can also be drawn through from the fluid conduit between FTC cartridge 300 and waste reservoir 1220.

In a post-hybridization routine, the syringe pump 1208 stops oscillating and forces any non-reacted test sample to waste. Then, the system can wash the FTC in the same manner as was done in pre-hybridization, after which imaging can take place on a separate piece of imaging equipment (not shown for simplicity).

Advantages of using an oscillation pumping scheme can include reduction of total hybridization volume (relative to a recirculation technique) resulting in higher test sample concentration (which can drive the reaction faster). Also, an oscillation pumping scheme can provide more efficient hybridization due to a greater number of "passes" through the FTC per unit time. In this regard, because the test sample can only hybridize when inside the microchannels of the FTC, and because diffusion can not occur between microchannels, the rate of test sample hybridization can be dependent on the number of passes made through the FTC.

As mentioned above, a flow-through device, such as the FTC, can be used in the FTC cartridge of the present invention. While the FTC can be used in a wide variety of assays, provided below are illustrative examples of the features and advantages of the FTC, and some of the types of assays in which FTC can be used.

For example, the FTC can be used as a "genosensor," where the binding reagent is an oligonucleotide or polynucleic acid that is immobilized in the channels of the substrate, and in which the analyte is a nucleic acid that is detected by hybridization (base pairing) to the binding reagent. Particular embodiments provide some or all of the following advantages (among others) over conventional devices for detecting binding reactions:

(1) improved detection sensitivity due to the vastly increased surface area of binding reagent to which the analyte is exposed. This increased area is due to the greater surface area of the channel surfaces compared to conventional devices where the binding agent is restricted to the two-dimensional surface of the device. The presence of the binding reagent on the inner surface of the channels running through the substrate greatly increases the quantity of the binding reagent present per unit of total two-dimensional substrate surface. In simple geometrical terms, for cylindrical channels of radius r extending between parallel surfaces of a substrate having a thickness h, the inner surface area is given by $\pi 2rh$. By contrast, for binding reagent confined only to the two-dimensional surface of a substrate, the surface area is given by $\pi r^2$.

Accordingly, for a single channel, the device of the invention can be considered to increase the surface area available for carrying binding reagent by a factor of $2h/r$. For a channel of radius 5 micrometers in a substrate 500-micrometer thick, this results in a 200-fold increase in the surface area. In a more complex example, where a group of channels of radius r contains n channels arranged in a circle of radius R, the two-dimensional area on the surface of the substrate is defined by $\pi R^2$, whereas the surface area inside the channels is given by $n\pi 2rh$. Accordingly, the increase in surface area is defined by the ratio: $n\pi 2rh/\pi R^2$.

Taking the above example, for instance, when r=5 and R=50 and there are 20 channels per group, this results in an increase in a 20-fold increase in the surface area.

(2) minimization of a rate-limiting diffusion step preceding the hybridization reaction (reducing the time required for the average target molecule to encounter a surface-tethered binding reagent or probe from hours to milliseconds, speeding hybridization and enabling mismatch discrimination at both forward and reverse reactions;

(3) improved analysis of dilute nucleic acid solutions by gradually flowing the solution through the channels in the wafer;

(4) enhanced recovery of bound nucleic acids from specific hybridization sites within the array, enabling further analysis of the recovered molecules;

(5) improved chemical bonding of probe molecules to the surface within the channels by avoiding the deleterious effect of rapid drying that occurs when small droplets of probe solution on flat surfaces are exposed to the atmosphere; and (6) confines the binding reagent within the channels, avoiding the problem where the binding reagent must somehow be prevented from spreading on a flat surface.

Accordingly, the FTC cartridge and fluidics station of the present invention provides an improved apparatus for the simultaneous conduct of a multiplicity of binding reactions on a flow through device having channels that run from a first to a second surface of the substrate. The channels can be subdivided and/or grouped into discrete and isolated regions defined by the presence or absence of particular binding reagents. A discrete and isolated region can comprise a single channel, or can comprise a collection of adjacent channels that defines a cognizable area on the surface of the substrate.

The groups of channels in each of the discrete and isolated regions can each contain an essentially homogeneous sample of a biomolecule of discrete chemical structure fixed in the channels. In this embodiment, each discyete and isolated region can be made to correspond to the location of a single binding reaction.

The substrate can contact a sample (hereinafter, the "test sample") suspected of containing one or more molecular species that specifically bind to one or more of the binding reagents. Detection of the regions where such binding took place yields a pattern of binding that characterizes or otherwise identifies the molecular species present in the test sample.

The present invention therefore encompasses devices for the conduction and detection of binding reactions. Such devices can be used to characterize or otherwise identify molecular species that bind to a particular binding reagent via essentially any mode of specific molecular binding, including known modes of binding and modes that will be discovered in the future. For example, the FTC cartridge can be used to detect: antibody-antigen and ligand-receptor binding; nucleic acid hybridization reactions, including DNA-DNA, DNA-RNA, and RNA-RNA binding; nucleic acid-protein binding, for example in binding of transcription factors and other DNA-binding proteins; and binding reactions involving intact cells or cellular organelles. The device can be used for DNA sequence analysis.

The present invention can be employed in many different analytical tasks, including nucleic acid sequence analysis by hybridization, analysis of patterns of gene expression by hybridization of cellular mRNA to an array of gene-specific probes, immunochemical analysis of protein mixtures, epitope mapping, assay of receptor-ligand interactions, and profiling of cellular populations involving binding of cell surface molecules to specific ligands or receptors immobilized within individual binding sites. Specifically, the invention is not limited to the nucleic acid analysis exemplified herein, but can equally be applied to a broad range of molecular binding reactions involving small molecules, macromolecules, particles, and cellular systems. See, for example, the uses described in PCT Published Application WO 89/10977.

Optical detection of fluorescent-labeled reporters also can be employed in detection. In traditional sequencing, a DNA base-specific fluorescent dye is attached covalently to the oligonucleotide primers or to the chain-terminating dideoxynucleotides used in conjunction with DNA polymerase. The appropriate absorption wavelength for each dye is chosen and used to excite the dye. If the absorption spectra of the dyes are close to each other, a specific wavelength can be chosen to excite the entire set of dyes. One particularly useful optical detection technique involves the use of ethidium bromide, which stains duplex nucleic acids. The fluorescence of these dyes exhibits an approximate twenty-fold increase when it is bound to duplexed DNA or RNA, when compared to the fluorescence exhibited by unbound dye or dye bound to single-stranded DNA. This dye is advantageously used to detect the presence of hybridized polynucleic acids.

Methods for attaching samples of substantially homogeneous biomolecules to the channels of the microapparatus are known in the art. One preferred method of doing so is to attach such biomolecules covalently to surfaces such as glass or gold films. For example, methods for attachments of oligonucleotide probes to glass surfaces are known. A primary amine is introduced at one terminus during the chemical synthesis thereof. Optionally, one or more triethylene glycol units can be introduced therebetween as spacer units. After derivatizing the glass surface in the confined region with epoxysilane, the primary amine terminus of the oligonucleotide can be covalently attached thereto.

Provided below are specific experiments used to illustrate some of the advantages of the FTC cartridge and hybridization system according to the present invention.

Experiment 1: Uniform Fluid Distribution

Reproducible assay performance can be highly dependent on the uniformity of fluid distribution across the FTC (or chip) face. To test the uniformity of fluid flow, the inventors performed two different sets of experiments.

Figure 12:
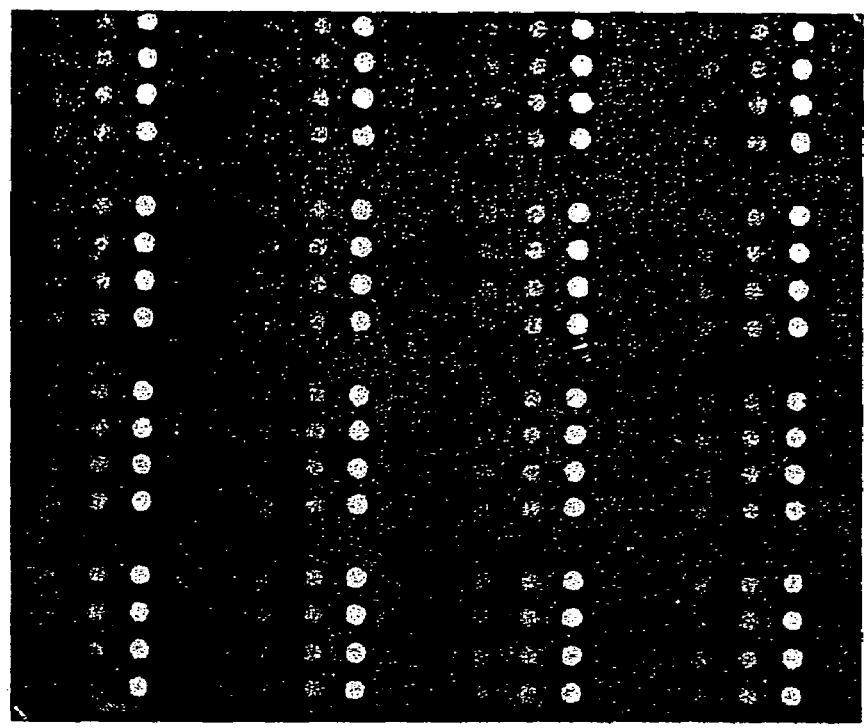
FIG. 12 shows an image taken of a hybridization assay illustrating the uniformity of hybridization using the FTC cartridge of FIG. 3.

In a first experiment, a microarray pattern was spotted covering 60% of the viewable chip area. The array consisted of 16 identical 4×4 subarrays. Each subarray contained 4 different probes, denoted as probes 1-4 (P1-P4), spotted in quadruplicate. An image of the uniformity test array run through the FTC is shown in FIG. 12. In this experiment, a FTC cartridge had a test fluid delivery chamber that included a spade-like flow surface, such as flow surface 421 illustrated in FIGS. 3 and 4. The FTC cartridge had an $\alpha_1$-angle slope of 2.55°, an $\alpha_2$-angle slope of about 3.7, and a trench $\beta$-angle of about 2.6°. The target mixture used to test the array contained targets complimentary to Probes 1, 2, and 3. The concentrations for targets 1, 2, and 3 were 2 nM, 10 nM, and 20 nM, respectively. The target to Probe 4 was left out as a control. The re-circulation flow rate was 0.2 mL/min. for a total hybridization period of four hours, conventional charge-coupled device (CCD camera) was used to image the signal emanating from the flow-through device.

The measured standard deviations were 14%, 12%, and 7% for Probe/Target pairs 1, 2, and 3, respectively. The small variability for each Probe/Target pair indicates that the fluid distribution is substantially uniform over the entire microarray. The standard deviations were noticeably smaller if the spots at the edge of the array are removed from the statistical sample set or by imaging subsections of the array individually. It is believed that the deviations calculated were thus slightly inflated, due to problems in the optical detection system used. In comparison, the measured standard deviation for a single probe in a FTC housed in a cell utilizing a flat back design was approximately 50%.

In a second experiment, an FTC microarray covering 100% of the exposed FTC first and second surfaces was hybridized to a synthetic DNA target and detected by fluorescence microscopy. As a basis for comparison, identical FTC microarrays were hybridized within a first test cartridge designed according to the embodiments of the invention (having the features described above) and a second test cartridge, which included a multi-port, flat-back flow cell. The second test cartridge lacked several important attributes found in the FTC cartridge according to the present invention. Results were compared by analyzing hybridization variability across all spots within the full array and within regional sub-grids of the array.

In particular, the architectural differences between the first and second test cartridges included: the position of inlets and outlets, the number of inlets and outlets, the sealing subsystem, the contour of the surface 421 (see e.g., FIGS. 4D and 5C) and the cartridge fastening mechanism. The first test cartridge was identical to the cartridge 300 containing the chip-holder 320 illustrated in FIG. 3. In contrast, the second test cartridge contained the following differences from the first test cartridge: 4 fluid inlets and 2 fluid outlets; inlet/outlet locations positioned parallel to one another on opposite sides of the chip-holder; a sealing subsystem consisting of a single rubber gasket interfaced only with the second surface of the FTC and allowing a metal interface with the first surface of the FTC; a flat chip-holder surface 421; and a non-uniform fastening mechanism that lacks the shoulder-screw 352/spring-washer 353 design. The results of multiple DNA hybridization assays conducted with the second and first cartridges demonstrate the combined effects of these design characteristics on hybridization uniformity.

In the experiment, 23 base pair single stranded DNA probes were spotted on FTCs in a 32×32 array (1024 spots) of 5 nanoliter (nl) volumes with 350 µm pitch. When sealed within the test cartridges, a 29×29 section of the full array covered 100% of the chip area exposed to fluid flow conditions (~10 mm²). Using a fluidics station embodying the features of fluidics station 800, arrays were hybridized to a complementary 23 base pair DNA target labeled with a fluorescein reporter molecule. Three sets of hybridization assays were conducted (I, II, and I) for 2 hours at room temperature at a 1 ml/min flow rate. Following hybridization, FTCs were imaged with a customized fluorescent microscope coupled to a CCD camera. Chips hybridized in the second cartridge were transferred to another FTC cartridge (similar to the first cartridge) to ensure that the imaging environment was identical for both test cartridge data. Identical optical conditions were used when imaging each set of chips.

Figure 15:
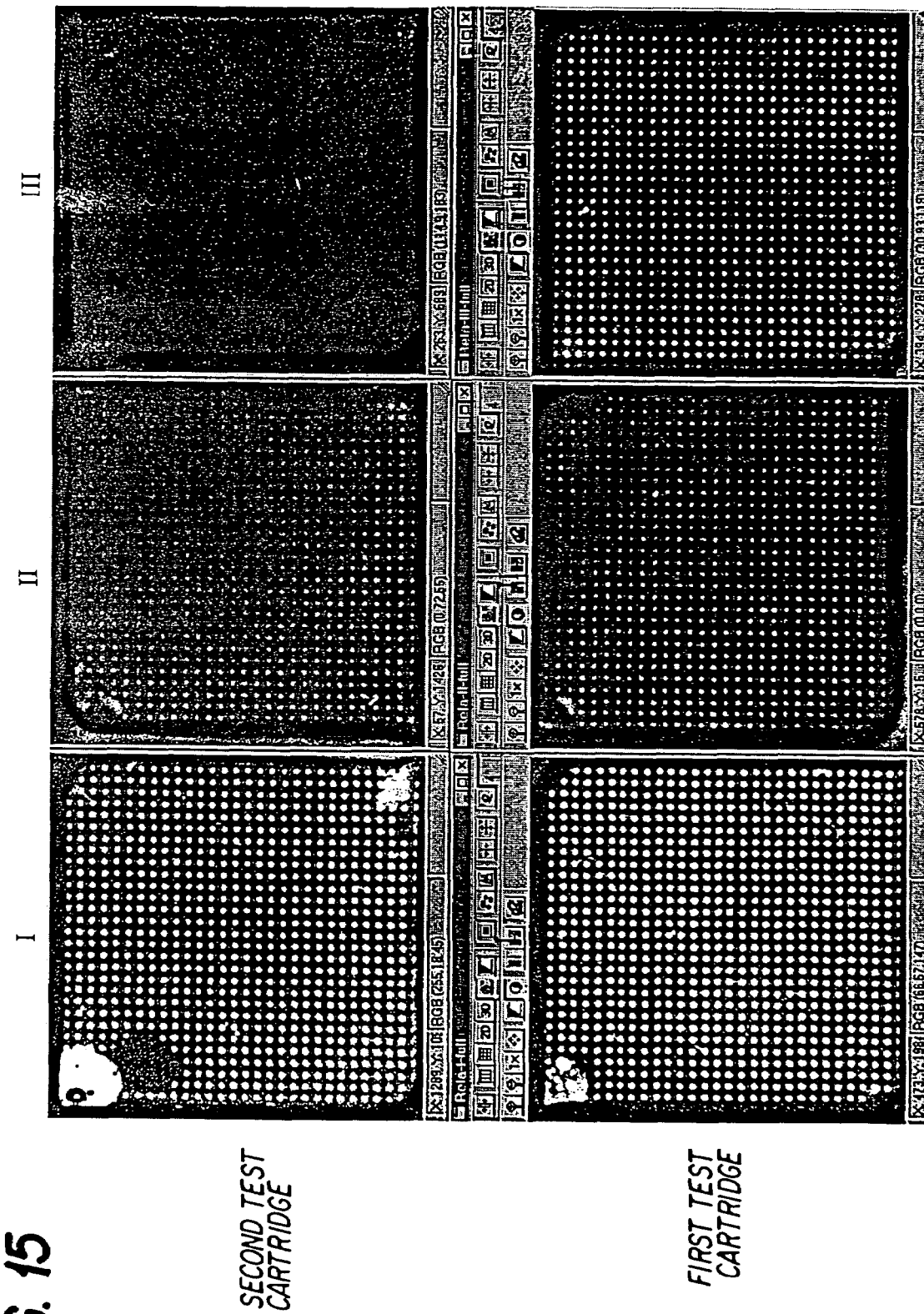
FIG. 15 shows image results for each set of hybridization experiments comparing a first test cartridge designed according to the present invention and a second test cartridge having a flat-back design and multiple inlets and outlets.

Image results for each set of hybridization experiments using the first test cartridge and the second test cartridge can be seen in FIG. 15. Each image was collected with a 5 second integration time and corrected for flat-field variations by subtracting an image of a blank FTC contained within an FTC cartridge. The same flat-field image was used for one set of experiments (i.e. either set I, II, or III). Quantitative information for each image can be found in Table 1. Each image was analyzed by cropping the first 4 rows and columns of spots, creating a 21×21 sub-grid (441 spots). This ensured that the comparison between hybridizations in the test cartridges was unbiased due to drastic edge effects caused by illumination and/or flat field correction. Any spots missing from the array were not included in the analysis. The average, standard deviation, and coefficient of variation (CV) of the background corrected hybridization signal are reported.

The CVs for hybridization uniformity across all three experiment sets range from 14% to 28% for the second cartridge and 7% to 23% for the first test cartridge. The first test cartridge shows an average improvement in uniformity of 1.7 times that of the second test cartridge. Furthermore, the overall fluorescence intensity between hybridizations within the second test cartridge is more variable than that of the first test cartridge. Average signal intensities between experiment sets range from 65% to 80% difference in the second test cartridge and 27% to 55% in the first test cartridge.

Quantitative data on hybridization uniformity within the test cartridges 1 and 2 is shown in TABLE 1. Three experiment sets were conducted with each cartridge and compared by average (Avg), standard deviation (St Dev), and coefficient of variation (CV).

TABLE 1

| Set | $Avg_{C1}$ | $Avg_{C2}$ | St $Dev_{C1}$ | St $Dev_{C2}$ | $CV_{C1}$ | $CV_{C2}$ |
| --- | --- | --- | --- | --- | --- | --- |
| I | 97557 | 62333 | 6807 | 9016 | 0.070 | 0.145 |
| II | 43674 | 21969 | 10147 | 6180 | 0.232 | 0.281 |
| III | 71418 | 12601 | 10428 | 3509 | 0.146 | 0.279 |

Experiment 2: In-situ Detection

An advantage of the FTC cartridge and fluid delivery system of the present invention is that it permits observation and/or detection of reactions in-situ. For example, DNA hybridizations were monitored for fluorescently labeled targets in real-time by mounting the FTC cartridge of the present invention on an epi-flourescence microscope. As sample passes through the chip, specific targets are captured from solution by the probes on the FTC. Under a recirculation condition, target accumulates over time resulting in greater fluorescence intensity. In-situ detection of hybridization to the FTC was investigated using the FTC cartridge 300 described above with respect to Experiment 1. The cartridge was interfaced with a fluidics station embodying the features of the fluidics station 800 illustrated in FIG. 11. The cartridge was placed on the stage of a fluorescent microscope for the duration of the hybridization in order to allow in-situ detection. The FTC within the cartridge was arrayed with 3 distinct oligonucleotide DNA probes and was hybridized to a sample pool of 3 complementary DNA targets (2033, 2139, 2373) for 6.25 hours in 1×SSPE at room temperature. The target was modified with a Fluorescein Isothiocyanate ("FITC") fluorescent reporter group to permit direct detection on the chip. The concentration of each target was 0.25 nM, 2.5 nM, and 25 nM for targets 2033, 2139, and 2373, respectively. During the course of the hybridization, flouurescent images were taken at 30 second time intervals for the first 5 minutes, followed by 60 second time intervals from the 5 minute mark until the end of the experiment. The resulting data was plotted in a graph of hybridization signal versus time and is shown in FIG. 16.

Figure 16:
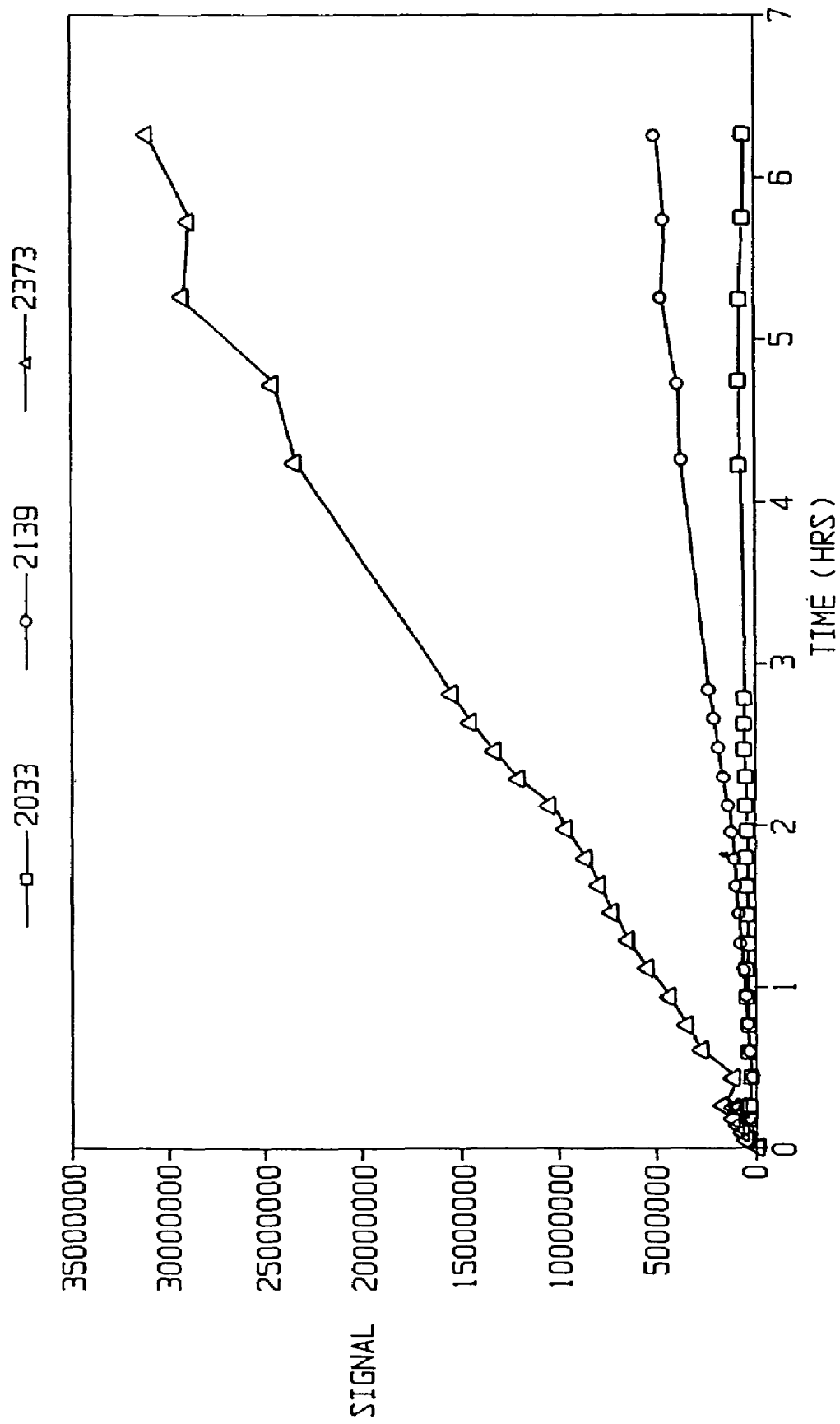
FIG. 16 shows a plot of hybridization signal versus time.

In FIG. 16, the plot of hybridization signal versus time (i.e., reaction rate) displays a linear trend for each of the three targets. Additionally, the plot of hybridization signal versus target concentration displays a linear trend. The quantitative relationship between the three target concentrations can be measured by comparison of either the slopes of signal versus time or by comparison of the signal versus the target concentration. In the first case, the correlation coefficient was $R^2=0.99$. In the second case, the correlation coefficient was $R^2=0.97$. Thus, quantitative measurements of relative target abundance can be made in-situ as well as in an end-point format.

In-situ hybridization measurements are an advantageous feature of the fluidics design for the FTC in comparison to typical hybridization measurements, which are taken at one point in time after hybridization. In-situ hybridization measurements can be used as an alternative method of simultaneously determining relative target abundance in a test sample for a large number of genes, which would be difficult without the fluidics station, cartridge design, and method of detection described herein. An alternative use for in-situ hybridization detection includes the measurement of hybridization as a function of temperature and time, which would allow highly resolved sequence discrimination between wild type gene sequences and gene sequences mutated at a single nucleotide polymorphism (SNP).

Experiment 3: Temperature Control of Hybridization

By way of background, there is a significant interest in using DNA chips to determine single nucleotide polymorphisms (SNPs) for diagnostics. SNPs are single base mutations that can contribute to diseases. Mapping of SNPs is conventionally performed to determine the role in disease development and progression. Once determined, the SNP can be used as a diagnostic marker for testing individuals. Within the nucleic acid sequence homology, a successful discrimination between perfectly-matched (PM) and single base pair mismatch (SBMM) sequences is difficult to detect because of the requirement for control of test conditions, including temperature.

The ability to discriminate PM and SBMM sequences was investigated using the FTC cartridge 300 (as described above with respect to Experiment 1) by varying the temperature during hybridization for a series of PM and mismatch probes. FTCs were prepared with 3 different 18 mer probes including a PM, SBMM, and a three-base mismatch (TBMM), in a similar manner to the procedures described above. The probes were complementary to a 65 mer sequence based on a segment of beta-actin mRNA (GenBank M17851). The target was modified with a Texas Red fluorescent reporter group to permit direct detection on the chip. The probes aligned to the first 18 bases of the target from the 5' end. The SBMM was created by inserting a pyrimidine for a purine, creating a pyrimidine-pyrimidine mismatch at the $10^{th}$ nucleotide on the PM sequence. The TBMM was created by similar modification at the $9^{th}$-$11^{th}$ nucleotides on the PM sequence. FTCs were hybridized to 1.2 picomoles of labeled target for 2 hours at a 700 microliters/min. flow rate. A fluidics station embodying the features of fluidics station 800 and a cartridge identical to the FTC cartridge described above with respect to Experiment 1 were used in all cases. Fluid temperature inside the cartridge was controlled during pre-hybridization, hybridization, and post-hybridization. Hybridizations were performed at 20, 25, 28, 35, 40, and 46° C. (±2° C.).

Figure 13:
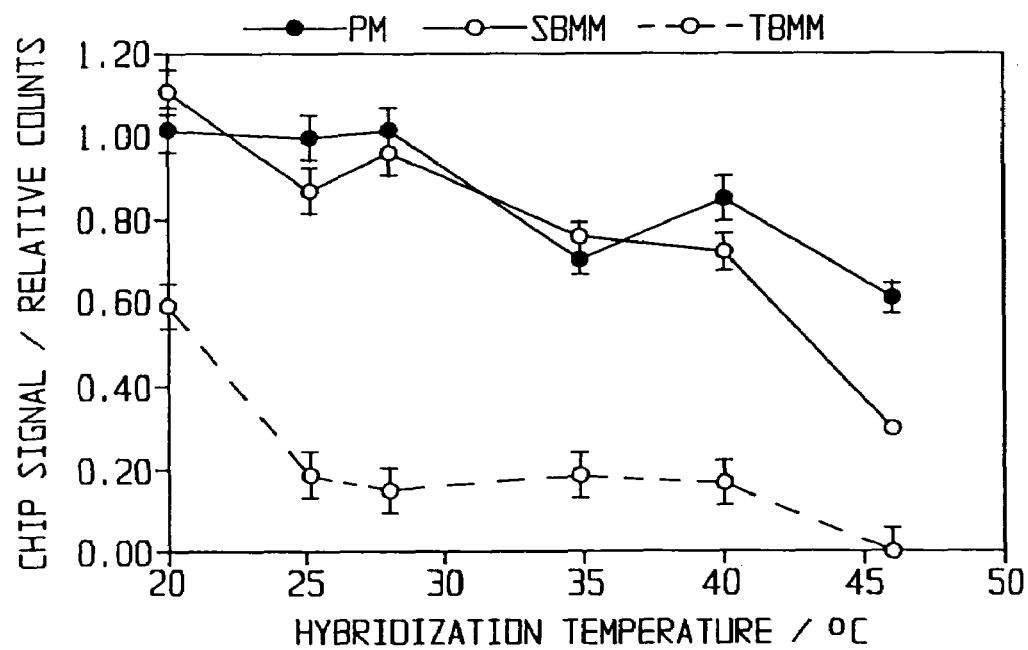
FIG. 13 shows a plot of FTC signal as a function of hybridization temperature.

FIG. 13 shows a plot of the fluorescence intensity for the PM (closed symbol/solid line), SBMM (open symbol/solid line), and TBMM (open symbol/dashed line) probe sets versus the hybridization temperature. The error bars represent 1 standard deviation on 3 readings from one assay at each temperature.

The intensity signal for the TBMM is initially below the other probes and falls off dramatically as the hybridization temperature is increased. The SBMM and PM show comparable results up to about 35° C. at which point the SBMM signal starts to decline at a faster rate than the PM signal. The experimental results are in qualitative agreement with solution melts for the probe/target pairs. The Tm's for the PM, SBMM, and TBMM in solution are 73° C., 63° C., and 49° C., respectively. The data indicates that hybridization temperature on the FTC need not reach the solution Tm temperature to provide the same level of discrimination. The data also indicates that near complete complementarity of probe and target is necessary to result in hybridization on the FTC. Control of the temperature within well-defined limits during hybridization was engineered into the integrated system and thus provides notable benefit for nucleic acid analyses, including SNPs.

Experiment 4: Reusability

As discussed above with respect to FIGS. 8 and 9A, the FTC cartridge and fluidics station facilitates the reusability of flow-through devices, which is beneficial for the quantitative analysis of sample analytes and for the efficiency of flow-through device assays. According to the embodiments of the invention, any reversible binding reaction that can be detected by a flow-through device also can be removed or "stripped" from the device such that the flow-through device can be reused in subsequent binding assays. In this way, the reusability of a flow-through device affords more accurate quantitative comparisons between sample analytes that would normally be analyzed by two or more replicate devices. Reusing a single flow-through device for multiple sample analytes eliminates the variability that naturally occurs between assays run on separate devices. Additionally, reusing a single flow-through device where multiple devices might otherwise be employed reduces the total number of devices necessary for a set of multiple assays, thereby increasing assay efficiency in terms of samples analyzed per device.

The ability to reuse a single FTC in multiple binding assays was investigated using an FTC cartridge (having the features of the FTC cartridge utilized in Experiment 1) by performing a series of DNA binding and stripping experiments. An FTC arrayed with 5 distinct oligonucleotide DNA probes was hybridized to a sample pool of 5 distinct complementary DNA targets for 1 hour in 5 × SSPE at room temperature. The target was modified with a Fluorescein Isothiocyanate ("FITC") fluorescent reporter group to permit direct detection on the chip. The probes aligned to within 18 and 24 bases of the target from the 5' end.

After hybridization, the FTC was imaged with a fluorescent microscope coupled to a CCD camera and then stripped of bound targets by flushing 65° C. deionized water through the FTC for 30 minutes. After stripping, the FTC was imaged again to display the removal of bound targets. The process of hybridization and stripping was repeated 3 times resulting in four separate hybridization reactions. All images were collected with identical CCD integration time and gain parameters.

Figure 14:
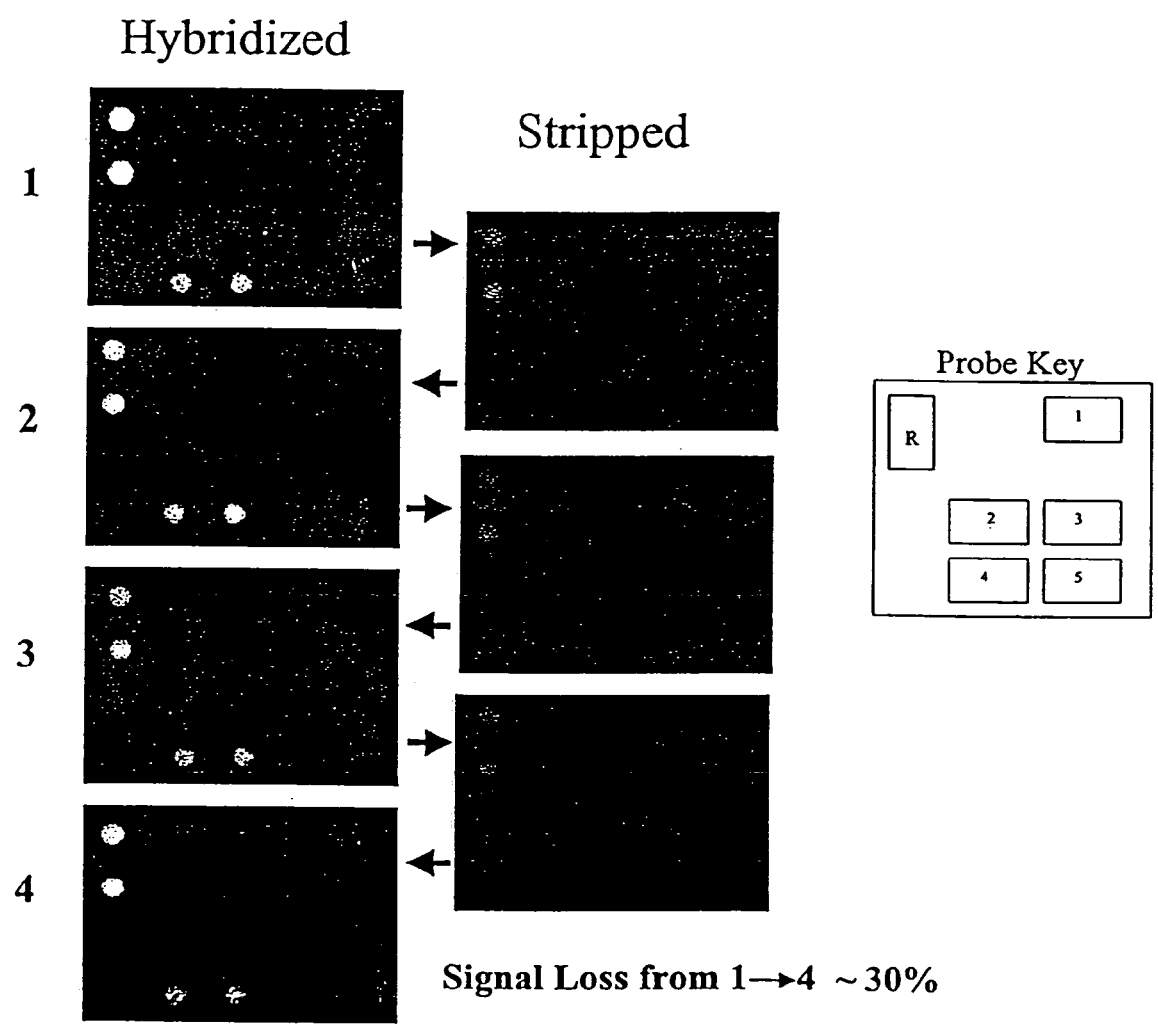
FIG. 14 shows images from the FTC reusability experiment.

Images from the FTC reusability experiment can be seen in FIG. 14. Arrows indicate the order of each hybridization and stripping experiment. The relative responses of the different probes are unchanged between assays 1 through 4. However, some degree of attenuation is observed after each subsequent hybridization. The average attenuation of the hybridization signal from assay 1 to assay 4 is approximately 30%. The reference signal, R, is a non-complementary probe with a fluorescent end-label that helps to localize the array after stripping. The difference in intensity of the reference signal in hybridization images versus stripped images is not dependent on hybridization, but rather on the imaging medium, which is either saline or deionized water.

The data suggest that a single FTC can be reused at least up to four times in conjunction with the FTC cartridge and fluidics station, with about 30% total signal attenuation and, importantly, very little change in relative quantitation between probes of differing complementarity. Control of the temperature and buffer salinity during the stripping process was engineered into the integrated system and thus provides notable benefit for quantitative nucleic acid analyses through FTC reusability.

While the present invention has been described in terms of a preferred embodiment as a holder or cartridge for a flow through device, such as the FTC, the present invention should not be limited thereto. The present invention can be used as a cartridge or holder for any flow-through devices for carrying out and detecting binding reactions, in which binding reagents (or "probes") are immobilized within channels densely packed in a solid substrate. The present invention can be used with any flow through device that includes a substrate containing a first and second surface, where the channels extend through the substrate from the first to the second surface. The first and second surfaces of the substrate can be planar or parallel, although non-planar and non-parallel surfaces can be used. Suitable substrate materials include microchannel or nanochannel glass and porous silicon, which can be produced using known microfabrication techniques. Binding to reagents in the flow-through devices can be detected by devices and methods that are well known in the art including, but not limited to, microfabricated optical and electronic detection components, film, charge-coupled-device arrays, camera systems and phosphor storage technology.

The flow through devices used with the present holder can overcome limitations inherent in current solid phase methods for detecting binding reactions by eliminating the diffusion-limited step in flat surface binding reactions, and by increasing the amount of binding reagent present per unit area of the two-dimensional surface on the face of the substrate. In addition, the cartridge of the present invention can be used as a component of a fluidics station for performing FTC assays.

The invention has been disclosed so that those skilled in the art will recognize that various modifications can be made to the present invention without departing from the spirit and scope thereof.

The disclosures of all publications cited above are expressly incorporated herein by reference in their.

What is claimed is:

1. A cartridge for housing a flow through device, comprising:
   a flow through device having a first side, a second side, and an array of microchannel passages extending through the first and second sides; and
   a chip holder for holding the flow through device, the chip holder comprising:
      a body with a support that supports the flow though device;
      a flow surface formed within the body, the flow surface facing the first side, wherein the flow surface is angled;
      a test fluid chamber defined at least by the flow surface and the first side, and configured to produce a substantially uniform flow of a test fluid mixture through the microchannel passages; and
      a first port communicating with the test fluid chamber for passing the test fluid mixture into the test fluid chamber; and
      a first seal contacting the first side to prevent leakage of the test fluid in the test fluid chamber.

2. The cartridge of claim 1, further including a base for supporting the chip holder.

3. The cartridge of claim 1, wherein the flow surface includes a trench that is sloped relative to the first side, from a first portion to a second portion of the flow surface, to provide a greater spacing at the first portion than at the second portion from the first side.

4. The cartridge of claim 3, wherein the first port is formed at the first portion and the trench has a slope of about 1° to about 4° relative to the first side.

5. The cartridge of claim 4, wherein the slope is about 2.55° relative to the first side.

6. The cartridge of claim 1, wherein the body has a second port for draining the test fluid mixture that has passed through the flow through device.

7. The cartridge of claim 1, wherein the first seal contacts a perimeter region of the flow through device on the first side to direct flow of the test fluid mixture though the flow through device and to prevent leakage of the test fluid mixture round the flow through device.

8. The cartridge of claim 1, further comprising a second seal in contact with perimeter regions of the second side of the flow through device to prevent leakage of the test fluid mixture.

9. The cartridge of claim 8, wherein the second seal has a channel to direct a flow of the test fluid mixture to the second port.

10. The cartridge of claim 8, wherein the first and second seals are made of Viton rubber.

11. The cartridge of claim 1, wherein the support comprises a first shelf disposed around the flow surface, and the seal is sandwiched between the first side and the first shelf.

12. The cartridge of claim 1, further including an observation window, which is supported on the body for viewing the second side of the flow through device.

13. The cartridge of claim 12, wherein the body has a second shelf disposed around the first shelf, the observation window being seated over the second shelf.

14. The cartridge of claim 1, further including a low scatter window disposed over the second side of the flow through device.

15. The cartridge of claim 2, further including a cover with an opening positioned over the second side for passage of an optical signal therethrough.

16. The cartridge of claim 15, wherein the base, the chip holder, and the cover are constructed from a metal coated with a low light scattering coating.

17. The cartridge of claim 15, wherein the base, the chip holder, and the cover are injection molded as one piece.

18. The cartridge of claim 15, wherein the base is coupled to the cover with a fastener.

19. The cartridge of claim 18, wherein the fastener comprises a plurality of shoulder screws and spring washers, the base having complementary threaded portions for receiving threaded portions of the shoulder screws.

20. The cartridge of claim 18, wherein the fastener comprises a latch.

21. The cartridge of claim 20, wherein the cover and the base are hinged opposite the latch.

22. The cartridge of claim 1, wherein the body has a recess formed on an opposite side of the flow surface, wherein the recess forms a thermal chamber for controlling the temperature of the test fluid in the test fluid chamber.

23. The cartridge of claim 2, wherein the base has a recess for receiving the chip holder and the body has a recess formed on an opposite side of the flow surface, the recesses forming a thermal chamber for controlling the temperature of the test fluid in the test fluid chamber.

24. The cartridge of claim 23, further including an insert positioned in the recesses and defines the thermal chamber, the insert isolating the thermal fluid within the thermal chamber to prevent the test fluid from contamination.

25. The cartridge of claims 23, wherein the recess of the base is complementary to a low-end portion of the chip holder.

26. The cartridge of claim 24, further including means for distributing a thermal fluid into the thermal chamber.

27. A chip holder for holding a flow through device having a first side, a second side, and an array of microchannel passages extending through the first and second sides, comprising:
 a body with a support adapted to support the flow though device;
 a flow surface formed within the body, the flow surface adapted to face the first side,
 wherein the flow surface is angled;
 a test fluid chamber defined at least by the flow surface and the first side upon supporting the flow through device, and configured to produce a substantially uniform flow of a test fluid mixture through the microchannel passages; and
 a first port communicating with the test fluid chamber for passing the test fluid mixture into the test fluid chamber, wherein the body has a recess formed on an opposite side of the flow surface, wherein the recess forms a thermal chamber for controlling the temperature of the test fluid in the test fluid chamber.

28. The chip holder of claim 27, wherein the flow surface includes a trench that is sloped relative to the first side, from a first portion to a second portion of the flow surface, to provide a greater spacing at the first portion than at the second portion from the first side.

29. The chip holder of claim 28, wherein the first port is formed at the first portion and the trench has a slope of about 1° to about 4° relative to the first side.

30. The chip holder of claim 29, wherein the slope is about 2.55° relative to the first side.

31. The chip holder of claim 27, wherein the body has a second port for draining the test fluid mixture that has passed through the flow through device.

32. The chip holder of claim 27, wherein the support comprises a first shelf disposed around the flow surface, the support being adapted to seat a seal, which is adapted to be sandwiched between the first side and the first shelf.

33. The chip holder of claim 32, wherein the body has a second shelf disposed around the first shelf, the second shelf being adapted to seat an observation window.

34. A system for performing hybridization assays, comprising:
 a cartridge for housing a flow through device, comprising:
  a flow through device having a first side, a second side, and an array of microchannel passages extending through the first and second sides;
  a chip holder for holding the flow through device, the chip holder comprising:
   a body with a support that supports the flow though device;
   a flow surface formed within the body, the flow surface facing the first side, wherein the flow surface is angled;
   a test fluid chamber defined at least by the flow surface and the first side, and configured to produce a substantially uniform flow of a test fluid mixture through the microchannel passages; and a first port communicating with the test fluid chamber for passing the test fluid mixture into the test fluid chamber; and a fluidics station for delivering the test fluid mixture to the cartridge.

35. The system of claim 34, further comprising a temperature controller for controlling the temperature of the test fluid in the test fluid chamber.

36. The system of claim 34, wherein the fluidics station comprises:

a pump for moving fluid through a fluid path;

a buffer selection valve for controlling a passage of buffer solutions from buffer reservoirs;

a sample injection valve for controlling the passage of a target or probe compound into the fluid path to form the test fluid mixture; and a re-circulation control valve in the fluid path and communicating with the buffer selection valve for controlling fluid flow, wherein the re-circulation valve is switchable between an open circuit mode and a closed circuit mode, wherein in the open circuit mode, the pump communicates with one or more of the buffer solutions to direct the buffer solutions through the sample injection valve and the cartridge, and wherein in the closed circuit mode, the pump flows the test fluid flow though the sample injection valve and the cartridge in a closed loop.

37. The system of claim 34, further comprising: a system controller for monitoring and controlling fluid delivery, timing, and temperature of the system.

38. The system of claim 34, wherein the flow surface includes a trench that is sloped relative to the first side, from a first portion to a second portion of the flow surface, to provide a greater spacing at the first portion than at the second portion from the first side.

39. The system of claim 38, wherein the first port is formed at the first portion and the trench has a slope of about 1° to about 4° relative to the first side.

40. The system of claim 39, wherein the slope is about 2.55° relative to the first side.

41. The system of claim 34, wherein the body has a second port for draining the test fluid mixture that has passed through the flow through device.

42. The system of claim 34, wherein the body has a recess formed on an opposite side of the flow surface, wherein the recess forms a thermal chamber for controlling the temperature of the test fluid in the test fluid chamber.

* * * * *